(12) United States Patent
Kalvins et al.

(10) Patent No.: US 8,889,902 B2
(45) Date of Patent: Nov. 18, 2014

(54) ACETYLSALICYLIC ACID SALTS

(75) Inventors: Ivars Kalvins, Ikskile (LV); Anatolijs Birmans, Riga (LV); Maris Veveris, Riga (LV); Antons Lebedevs, Riga (LV); Anatolijs Misnovs, Riga (LV)

(73) Assignee: Tetra, SIA, Riga (LV)

( * ) Notice: Subject to any disclaimer, the term of this patent is extended or adjusted under 35 U.S.C. 154(b) by 156 days.

(21) Appl. No.: 13/377,926

(22) PCT Filed: Jun. 21, 2010

(86) PCT No.: PCT/LV2010/000007
§ 371 (c)(1),
(2), (4) Date: Dec. 13, 2011

(87) PCT Pub. No.: WO2010/151095
PCT Pub. Date: Dec. 29, 2010

(65) Prior Publication Data
US 2012/0088742 A1    Apr. 12, 2012

(30) Foreign Application Priority Data

Jun. 25, 2009 (LV) ..................... P-09-117
Jun. 21, 2010 (LV) ..................... P-10-95

(51) Int. Cl.
| | | |
|---|---|---|
| C07C 65/10 | (2006.01) |
| C07C 69/157 | (2006.01) |
| C07C 229/22 | (2006.01) |
| C07C 229/12 | (2006.01) |
| C07C 243/40 | (2006.01) |
| A61K 31/616 | (2006.01) |

(52) U.S. Cl.
CPC ............. *C07C 229/12* (2013.01); *C07C 69/157* (2013.01); *C07C 229/22* (2013.01); *C07C 243/40* (2013.01); *A61K 31/616* (2013.01)
USPC ........................... 562/477; 514/161; 424/499

(58) Field of Classification Search
None
See application file for complete search history.

(56) References Cited

U.S. PATENT DOCUMENTS

| | | | | |
|---|---|---|---|---|
| 4,265,888 | A * | 5/1981 | Kagitani et al. .............. | 514/162 |
| 5,227,513 | A * | 7/1993 | Meul .............................. | 560/66 |
| 7,223,797 | B2 * | 5/2007 | Kalvinsh et al. .............. | 514/556 |
| 8,063,243 | B2 * | 11/2011 | Franckowiak et al. ....... | 562/477 |

FOREIGN PATENT DOCUMENTS

| | | |
|---|---|---|
| DE | 198 39 443 | 3/2000 |
| WO | WO 2006/128600 | 12/2006 |
| WO | WO 2007/021164 | 2/2007 |

OTHER PUBLICATIONS

International Preliminary Report on Patentability for PCT/LV2010/000007 of Nov. 4, 2010.
International Search Report for PCT/LV2010/000007 of Aug. 25, 2010.

* cited by examiner

*Primary Examiner* — Sudhakar Katakam
(74) *Attorney, Agent, or Firm* — Hueschen and Sage

(57) ABSTRACT

Novel betaine salts of acetylsalicylic acid, namely 4-trimethylammoniobutanoate acetylsalicylic acid addition salt (gamma-butyrobetaine acetylsalicylate), L-carnitine acetylsalicylic acid addition salt and 3-(trimethylammonioamino) propanoate (meldonium) acetylsalicylic acid addition salt. Use of meldonium acetylsalicylate as antiplatelet agent for treating various pathologies induced by platelet aggregation, anti-inflammatory and antihyperlipidemic agent.

8 Claims, 1 Drawing Sheet

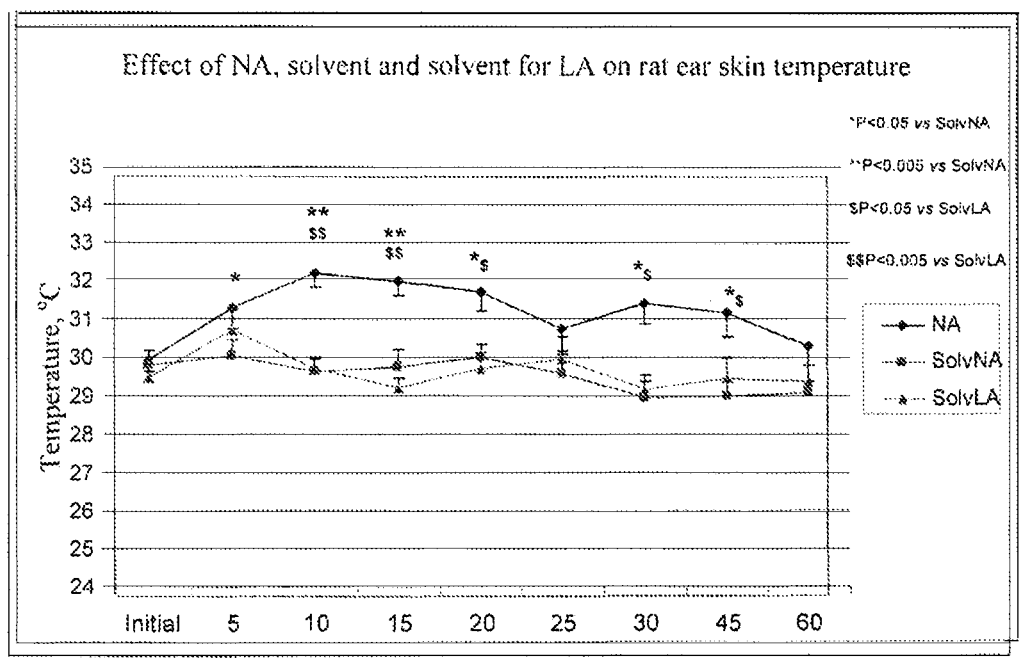

ACETYLSALICYLIC ACID SALTS

FIELD OF INVENTION

The present invention relates in general to acetylsalicylic acid salts, and in particular to a new and useful water soluble acetylsalicylic acid salts and the method of making the same. Acetylsalicylic acid is a most widely used drug, known chiefly for its analgesic properties. Its range of application is greatly reduced by its low solubility in water (about 0.3%). Besides Li, Na, Mg and Ca salts a number of salts with basic amino acids (U.S. Pat. No. 4,265,888) had been disclosed. Each of these salts has certain advantages and shortcomings, it would therefore be advantageous to have available new salts of acetylsalicylic acid with potentially more advantageous properties.

Since betaine type compounds incorporated in the new salts of acetylsalicylic acid have various pharmacological activities themselves, the new salts of acetylsalicylic acid may have additional beneficial properties to those of acetylsalicylic acid or betaines, including new pharmacological activities.

OBJECT OF THE INVENTION

The object of this invention is the discovery of novel type acetylsalicylic acid salts with certain betaine type compounds. It was unexpected and surprising to discover that acetylsalicylic acid salts with certain betaines that themselves are hygroscopic substances yields stable, water soluble crystalline salts.

Accordingly, an object of the present invention is to provide acetylsalicylic acid salts that are highly soluble in water yet have outstanding stability and shelf life.

A further object of the present invention is to provide a method for making said salts.

Another object of the present invention is to provide meldonium acetylsalicylate (3-(trimethylammonioamino)propanoate acetylsalicylic acid addition salt) for use as medicament.

It is an object of the present invention to provide a medicinal product, namely 3-(trimethylammonioamino)propanoate acetylsalicylic acid addition salt (meldonium acetylsalicylate) with antiinflammatory, analgesic, antipyretic, antirheumatic, antihyperlipidemic, antiatherosclerotic, antiaggregative and antithrombotic properties. Another object of the present invention is a method of treating a subject in need of antiinflammatory, analgesic, antipyretic, antirheumatic, antihyperlipidemic, antiatherosclerotic, antiaggregative and antithrombotic therapy. An additional object of the invention is the provision of a pharmaceutical composition comprising MASA for the aforesaid purpose. Further objects of the invention will become apparent hereinafter, and still others will be obvious to one skilled in the art.

BRIEF DESCRIPTION OF THE DRAWINGS

FIG. 1 shows the effect of NA, solvent and solvent for LA on rat ear skin temperature.

DESCRIPTION OF THE PREFERRED EMBODIMENTS

The following are examples of various salts and methods of the present invention and their properties.

Example 1

4-trimethylammoniobutanoate Acetylsalicylic Acid Addition Salt

γ-Butyrobetaine dihydrate (1.81 g, 10 mmol) and acetylsalicylic acid (1.80 g, 10 mmol) were dissolved in ethanol (20 ml). The solution was concentrated in vacuo at about 40° C. till syrup consistence that on cooling crystallizes. The crystalline mass was triturated with acetone (50 ml), filtered, washed with acetone and dried in vacuo at room temperature. The yield of colorless crystals with m.p. 120-122° C. was 3.04 g (93.5%). The substance is water soluble, stable at ambient conditions.

$^1$NMR spectrum ($D_2O$, TMS) δ: 1.93-2.12 (2H, m, $CH_2\underline{CH_2}CH_2$); 2.33 (3H, s, $COCH_3$); 2.40 (2H, t, J=7.0 Hz, $\underline{CH_2}COO^-$); 3.09 (9H, s, $Me_3N$); 3.24-3.37 (2H, m, $CH_2N$); 7.16 (1H, dd, J=1.1 and 8.1 Hz, H-3); 7.38 (1H, ddd, J=1.1, 7.6 and 7.6 Hz, H-5); 7.56 (1H, ddd, J=1.8, 7.6 and 8.1 Hz, H-4); 7.79 ppm (1H, dd, J=1.8 and 7.6 Hz, H-6).

$C_{16}H_{23}NO_6$. Calculated, %: C 59.07; H 7.13; N 4.30.
Found, %: C 59.17; H 7.20; N 4.23.

The new salt is characterized by X-ray powder pattern (Cu $K_α$-radiation) having peaks at 2Θ-angles 5.10, 13.58, 13.83, 15.02, 15.17, 17.89, 19.33, 19.87, 21.85, 22.05, 23.32, 23.56, 23.92, 24.75, 25.55, 25.80, 27.05, 27.91, 30.25±0.2°.

Structure of the new salt is confirmed by means of X-ray single crystal structure analysis (below). Crystals are monoclinic, cell parameters at experiment temperature T=−85° C. are: a=13.2154(6) Å, b=7.5092(3) Å, c=17.6451(9) Å, β=104.728(2), cell volume V=1693.5(1) Å$^3$, space group $P2_1/a$. Fragment of 4-trimethylammoniobutanoate acetylsalicylic acid addition salt crystal structure:

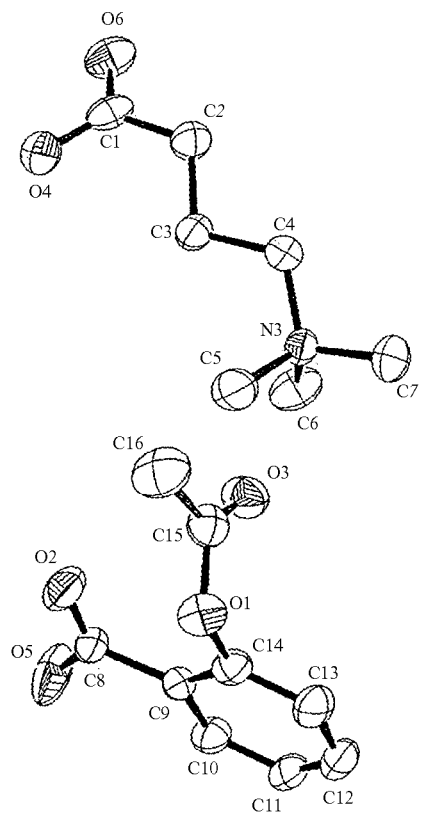

Example 2

L-carnitine Acetylsalicylic Acid Addition Salt

L-Carnitine (1.61 g, 10 mmol) and acetylsalicylic acid (1.80 g, 10 mmol) were dissolved in ethanol (20 ml) and the solution concentrated in vacuo at about 40° C. till syrup consistence that on cooling crystallizes. The crystalline mass was triturated with acetone (50 ml), filtered, washed with acetone and dried in vacuo at room temperature. The yield of colorless crystals with m.p. 90-94° C. was 3.17 g (93%). The substance is water soluble, stable at ambient conditions.

$^1$H NMR spectrum (D$_2$O, TMS) δ: 2.32 (3H, s, COCH$_3$); 2.53 (2H, d, J=6.6 Hz, CH$_2$COO$^-$); 3.18 (9H, s, Me$_3$N); 3.38-3.45 (2H, m, CH$_2$N); 4.59 (1H, quint., J=6.1 Hz, C HOH); 7.15 (1H, dd, J=1.1 and 8.1 Hz, H-3); 7.37 (1H, ddd, J=1.1, 7.6 and 7.6 Hz, H-5); 7.56 (1H, ddd, J=1.8, 7.8 and 7.8 Hz, H-4); 7.79 ppm (1H, dd, J=1.8 and 7.8 Hz, H-6).

C$_{16}$H$_{23}$NO$_7$. Calculated, %: C 56.30; H 6.79; N 4.10. Found: %: C 55.67; H 6.85; N 4.12.

The new salt is characterized by X-ray powder pattern (Cu K$_\alpha$-radiation) having peaks at 2Θ-angles 5.09, 12.62, 13.48, 13.84, 15.04, 17.82, 19.15, 19.77, 21.84, 22.56, 23.33, 23.92, 24.40, 25.17, 25.43, 26.14, 27.24, 29.50, 30.36±0.2°.

Structure of the new salt is confirmed by means of X-ray single crystal structure analysis (below). Crystals are monoclinic, cell parameters at experiment temperature T=−85° C. are: a=13.1342(6) Å, b=7.6396(3) Å, c=17.737(1) Å, β=104.535(2), cell volume V=1722.8(2) Å$^3$, space group P2$_1$. Fragment of L-carnitine acetylsalicylic acid addition salt crystal structure:

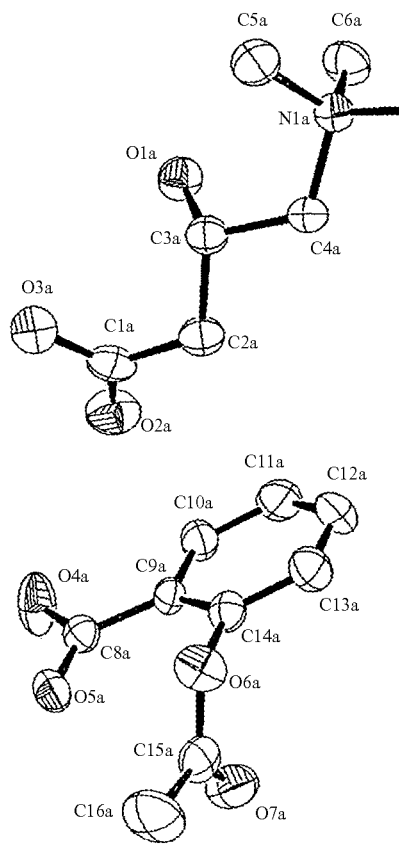

Example 3

3-(trimethylammonioamino)propanoate Acetylsalicylic Acid Addition Salt (Meldonium Acetylsalicylate)

3-(Trimethylammonioamino)propanoate dihydrate (INN-Meldonium) (3.64 g, 20 mmol) and acetylsalicylic acid (3.60 g, 20 mmol) were dissolved in hot propanol-2 (30 ml) and heated at 50-55° C. for 20 minutes. Heating was discontinued and solution stirred at room temperature for 3 h. The slurry was further stirred at 0° C. for another 3 h, precipitates were filtered off and washed with cold propanol-2 (2×15 ml). Desired salt was recrystallized from propanol-2. Colorless crystals were obtained with m.p. 104-106° C. Yield 4.12 g (63%).

$^1$H NMR spectrum (D$_2$O, TMS) δ: 2.34 (3H, s, COCH$_3$); 2.51 (2H, t, J=6.4 Hz, CH$_2$COO$^-$); 3.26 (2H, t, J=6.4 Hz, CH$_2$N); 3.33 (9H, s, Me$_3$N); 7.17 (1H, dd, J=1.1 and 7.8 Hz, H-3); 7.39 (1H, ddd, J=1.1, 7.6 and 7.6 Hz, H-5); 7.58 (1H, ddd, J=1.7, 7.6 and 7.8 Hz, H-4); 7.81 ppm (1H, dd, J=1.7 and 7.6 Hz, H-6).

C$_{15}$H$_{22}$N$_2$O$_6$. Calculated, %: C 55.21; H 6.79; N 8.58. Found, %: C 55.25; H 6.79; N 8.53.

The new salt is characterized by X-ray powder pattern (Cu K$_\alpha$-radiation) having peaks at 2Θ-angles 5.19, 13.22, 13.82, 14.20, 14.95, 15.36, 15.93, 18.11, 18.97, 19.74, 21.02, 22.15, 23.15, 23.65, 24.31, 25.28, 26.18, 26.58, 27.73, 28.36±0.2°.

Structure of the new salt is confirmed by means of X-ray single crystal structure analysis (below). Crystals are monoclinic, cell parameters at experiment temperature T=−85° C. are: a=19.3399(8) Å, b=7.2400(3) Å, c=35.237(2) Å, β=90.758(2), cell volume V=4933.5(4) Å$^3$, space group P2$_1$/n. Fragment of 3-(trimethylammonioamino)propanoate acetylsalicylic acid addition salt crystal structure:

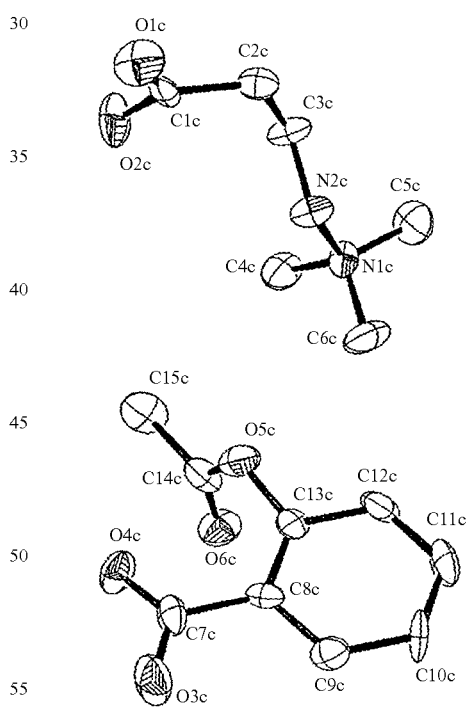

X-Ray single crystal diffraction data unambiguously show that carboxyl groups of 3,3,3-trimethylammoniumbutyric acid, L-carnitine and 3-(trimethyl-ammonioamino)-propionic acid in crystal structures are protonated thus showing proton transfer from acetylsalicylic acid and salt formation. Bond length values C=O and C—O in carboxyl groups are 1.215 Å and 1.305 Å respectively for 3,3,3-trimethyl-ammoniumbutyric acid acetylsalicylic acid addition salt crystal structure, 1.194 Å and 1.308 Å for L-carnitine acid acetylsalicylic acid addition salt crystal structure and 1.219 Å and 1.321 Å for 3-(trimethylammonioamino)propionic acid acetylsalicylic acid addition salt crystal structure. In turn for all three crystal structures carboxyl group C=O and C—O bonds of acetylsalicylic acid fragment are equalized and have values around 1.26 Å.

Pharmacological properties of 3-(trimethylammonioamino) propanoate acetylsalicylic acid addition salt (meldonium acetylsalicylate).

It is envisaged that the novel substance disclosed in the said application can appear in various polymorphic crystal forms and solvates, preferably hydrates that have similar biological properties and therefore included in this application as variants of the described compound.

We have initially established that meldonium acetylsalicylate delayed and significantly reduced the cutaneous vasodilation caused by niacin. Further experiments demonstrated surprising improved pharmacological activities of meldonium acetylsalicylate.

Abbreviations Used

The following abbreviations will be used further on in the description for shortness:

AdA—adjuvant arthritis
ASA—acetylsalicylic acid
C—cholesterol
CHD—coronary heart disease
CIC—circulating immune complexes
CL—clopidogrel
CRP—C-reactive protein
DI—dipyridamole
HDL—high density lipoprotein-cholesterol
LA—laropiprant
LDL—low density lipoprotein-cholesterol
MASA—meldonium acetylsalicylate (chemically: 3-(trimethylammonioamino)-propanoate acetylsalicylic acid addition salt)
MD—meldonium (INN)
NA—nicotinic acid, niacin
RA—rheumatoid arthritis
TG—triglyceride
TR—Triton WR1339
WBC—white blood cells
Substances.

NA (Acros Chemicals), MD (Grindex), ASA (Acros Chemicals), LA (MK 0524, Cayman Chemicals), CL for in vivo tests as Plavix™ (Sanofi-Aventis), DI (Sigma-Aldrich).

Background.

Acetylsalicylic acid is a most widely used drug, best known for its antiinflammatory, analgesic, antipyretic and antirheumatic properties. It is also used in small daily doses as antiplatelet agent for cardiovascular risk patients (Eidelman R S et al, *Arch Intern Med.* 2003; 163:2006-2010). Blood platelets play a pivotal role in the development of atherosclerosis and fatal thrombus formation in the course of coronary heart disease. Antiplatelet agents have become paramount in the prevention and management of various diseases involving the cardiovascular, cerebrovascular, and peripheral arterial systems (Meadows T A et al, *Circ Res* 2007; 100(9):1261-75). Although known for many years to be an antiplatelet agent, ASA is now becoming more recognized for its anti-inflammatory properties (Ridker P M et al, *N Engl J Med* 1997; 336:973-979) in cardiology. Accordingly, clinical measurements of such inflammatory markers as C-reactive protein (CRP) may in part reflect indices of atherosclerosis (Buckley D I et al, *Ann Intern Med* 2009; 151:483-495). Present evidence points to that reducing CRP levels prevents CHD events (Ridker P M et al, Lancet 2009; 373:1175-82). Ross proposed that atherosclerosis was an inflammatory disease (Ross R, *N Engl J Med* 1999; 340:115-126). ASA not only may address the inflammatory aspect of atherosclerosis but also may contribute directly by inducing hypolipidemia (Kourounakis A P et al, *Experimental and Molecular Pathology* 2002, 73:135-138).

NA is an effective lipid-altering agent that prevents atherosclerosis and reduces cardiovascular events. NA has multifarious lipoprotein and anti-atherothrombosis effects that improve endothelial function, reduce inflammation, increase plaque stability, and diminish thrombosis (Rosenson R S, *Atherosclerosis* 2003; 171:87-96)

NA almost totally prevented intravascular clotting induced by thromboplastin and pituitrin, showing that it has a thrombolytic effect (Baluda V P, *Kardiologija* 1974; 14(11):105-7 (Rus). Anti-thrombotic properties of NA are described by several authors (Shestakov V A, *Probl Gematol Pereliv Krovi,* 1977; 22(8):29-35. Chekalina S I, *Sov Med* 1982(5):105-8). Niacin reduces risk of blood clots (Chesney C M et al, *Am Heart J,* 2000; 140:631-36).

NA inhibit platelet aggregation (Lakin K M, Farmakol Toksikol, 1980; 43(5):581-5). NA in vitro affects platelet activity by mildly inhibiting aggregation, and stimulating significant prostaglandin release, with mostly intact major platelet receptor expression. The effect of NA is unique, differs from other known antiplatelet agents, and suggests potential opportunities for therapeutic combination (Serebruany V L et al, *Thrombosis and Haemostasis,* 2010 (in press).

NA is an effective lipid-altering agent that prevents atherosclerosis and reduces cardiovascular events (Drexel H, *European Heart Journal Supplements* 2006; Vol 8, Suppl F: F23-F29. Savel'ev A A, Shershevskii M G, *Klin Med (Rus)* 1996; 74:48-52).

NA is available in 3 formulations (immediate release, extended release, and long acting). Immediate-release NA is associated with adverse flushing and elevations in blood glucose levels. Long-acting NA is associated with reduced flushing, but also with risk of hepatotoxic effects. Extended-release is associated with less flushing and low hepatotoxic risk (McKenney J, *Arch Intern Med* 2004; 164(7):697-705).

The clinical use of NA has been limited by cutaneos flushing. Extended-release niacin can help to control flushing events (Guyton J R et al, *J Clin Lipidol,* 2009; 3:101-108). ASA and other NSAIDs have been proposed for control of flushing with different pharmaceutical compositions to ensure advance application of NSAIDs before the dosage of NA (WO9632942, WO9906052, WO2009142731).

Recently a specific antagonist to prostaglandin D2 (Parhofer K G, *Vascular Health and Risk Management* 2009; 5:901-908) receptor subtype 1, laropiprant, was proposed as agent for reducing NA-induced flushing (Lai E et al, *Clin Pharm Ther* 2007; 81:849-857. Davidson M H, *Am J Cardiol* 2008; 101 [suppl]:14B-19B). Although the addition of laropiprant will reduce the frequency of flushing, it will not completely eliminate this side effect. Laropiprant does not change the effect of niacin on lipids or other side effects of niacin. The combination of niacin with laropiprant may therefore enable use of niacin at higher doses and therefore exploit the full potential of the drug (Parhofer K G, *Vascular Health and Risk Management* 2009; 5:901-908, Olsson A G, *Expert Opinion on Pharmacotherapy* 2010; 11(10):1715-1726).

MD is a medicine with certain beneficial effects on heart and vessels. A certain desirable activity of MD was discovered in animal models of atherosclerosis (Veveris M, Smilsaraja B, *Baltic J Lab Anim Sci* 2000; 10,194-199. Veveris M et al., *Baltic J Lab Anim Sci* 2002; 12:116-122. Okunevich I V, Ryzhenkov V E, *Patol Fiziol Eksp Ter* 2002; (2):24-7), and observed in clinics (Karpov R S et al, *Ter Arkh* 1991; 63(4): 90-3). It has been also noticed that MD inhibits platelet aggregation (Tsirkin V I, *Ros Kardiol Zh* 2002; 1:45-52). Two weeks long therapeutic use of MD peroral administration in rabbits and dogs after experimental arterial thrombosis showed trombolytic effect (Logunova L et al, *Experim Clin Pharmacoter* 1991; 19:91-98 (Rus). No data on prophylactic effect of MD on limitation or prevention of thrombosis are known.

Example 4

Determining Acute Toxicity of MASA

The acute toxicity of MASA was determined on Wistar rats and ICR mice by p.o. introduction.
Methods.

Male IRC mice with body mass of 20-22 g and Wistar rats with body mass of 200-230 g were used. For determining the acute toxicity each dose was given to 6 animals, each next dose was increased by 500 mg/kg. $LD_{50}$ was calculated after Karber by the method of Akhila J S et al, *Current Sci* 2007; 93:917-920 with modification for determining the dose confidence interval (Turner R In *Screening Methods in Pharmacology*, Acad. Press, New York, 1965, 61-63).
$LD_{50}$ was calculated as follows:

$LD_{50}$=Least dose lethal to all in a group$-\Sigma(a \times b)/N$

N—number of animals in each group
a—the dose difference
b—the mean mortality (lethality in 2 neighbouring groups/2)

MASA was dissolved ex tempore in 0.2% agar-agar and introduced per os through catheter into stomach. The volume of liquid thus introduced did not exceed 0.5 ml for mice and 2 ml for rats. Animals were observed till the Day 10 after introduction.
Results.

Results for MASA acute toxicity to mice are represented in Table 1 and Table 2.

TABLE 1

MASA acute toxicity to mice p/o

| Group | Dose mg/kg p.o. | Number of animals in group (N) | Lethality (n) | Mean mortality (b) | Probit (a × b) |
|---|---|---|---|---|---|
| 1 | 1000 | 6 | 0 | | |
| 2 | 1500 | 6 | 1 | 0.5 | 250 |
| 3 | 2000 | 6 | 2 | 1.5 | 750 |
| 4 | 2500 | 6 | 4 | 3 | 1500 |
| 5 | 3000 | 6 | 6 | 5 | 2500 |

$LD_{50} = 3000 - (5000/6) = 2167$
Factor f at P = 0.05 for this experiment is 1.32, therefore the confidence interval for $LD_{50}$ is 1642-2860 (mg/kg).

After the introduction of MASA the toxic effects appeared within the first hours and a part of animals died within the first 2 days. The toxicity symptoms in surviving animals gradually subsided and after 5-8 days these animals were not different from the controls of the same age. Thus $LD_{50}$ of MASA for mice p.o. is found to be 2167 (1642÷2860) mg/kg.
Results for the acute toxicity of MASA in rats p.o. are presented in Table 2 and Table 3.

TABLE 2

Acute toxicity of MASA to rats p.o.

| Group | Dose mg/kg | Number of animals in group (N) | Lethality (n) | Mean mortality (b) | Probit (a × b) |
|---|---|---|---|---|---|
| 1 | 1500 | 6 | 0 | | |
| 2 | 2000 | 6 | 2 | 1 | 500 |

TABLE 2-continued

Acute toxicity of MASA to rats p.o.

| Group | Dose mg/kg | Number of animals in group (N) | Lethality (n) | Mean mortality (b) | Probit (a × b) |
|---|---|---|---|---|---|
| 3 | 2500 | 6 | 4 | 3 | 1500 |
| 4 | 3000 | 6 | 6 | 5 | 2500 |

$LD_{50} = 3000 - (4500/6) = 2250$
Factor f at P = 0.05 for this experiment is 1.308, therefore the confidence interval for $LD_{50}$ is 1720 ÷ 2944 (mg/kg).

Introduction of MASA to rats p.o. in dose 1500 mg/kg caused transient disturbances in feeding habits and movements, but all animals survived. The toxic symptoms started to disappear from day 3 after introduction. Thus $LD_{50}$ of MASA for rats p.o. is found to be 2250 (1720÷2944) mg/kg.
Summary.

The acute toxicity studies indicated that MASA is a substance of low toxicity ($LD_{50}$>2000 mg/kg p.o. for mice and rats). Acute toxicity for ASA is given by Boehringer Ingelheim Pharmaceuticals, Inc., Acros Chemicals and Sigma-Aldrich as 250 mg/kg for mice and 200 mg/kg for rats p.o., while Bayer AG gives $LD_{50}$ for rats p.o. as >1100 mg/kg and thus MASA is less toxic than ASA.

Acute toxicity of MASA for mice and rats; N = 6.

| Animals | LD50 mg/kg p.o. (confidence interval) |
|---|---|
| Mice | 2167 (1642 ÷ 2860) |
| Rats | 2250 (1720 ÷ 2944) |

Example 5

Investigation of Analgesic, Antipyretic and Anti-Inflammatory Activity of MASA in Comparative Experiments with ASA and MD In investigating the analgesic, anti-inflammatory and antipyretic effects of MASA methods widely used in evaluation of NSAIDs were employed. Mongrel white laboratory mice and Wistar rats were used in experiments. Animals were kept in groups of 7-8 in adequate cages in climatized rooms at 22±1° C., relative humidity 60±5% and 12/12-hour light/darkness cycle with free access to feed and water.
The following groups were formed for comparing the effects of MASA with ASA and MD by oral route:

| GROUP | TREATMENT |
|---|---|
| ASA50 | received ASA 50 mg/kg |
| ASA100 | received ASA 100 mg/kg |
| MD100 | received MD 100 mg/kg |
| MASA75 | received MASA 75 mg/kg |
| MASA150 | received MASA 150 mg/kg |
| MASA300 | received MASA 300 mg/kg |

Aqueous solutions of test substances were prepared ex tempore. In each experimental series a control group was used that received an identical volume of water p.o.
Statistics.

Data were analyzed by Microsoft Excel 2007 software and results expressed as Mean±SEM. Mean results of different groups were compared using single-factor analysis according to ANOVA with repeated comparison (Tukey's test). $P<0.05$ was considered as significant.

5.1. Investigation of Analgesic Activity
5.1.1. Evaluation of Analgesic Activity by Mouse Writhing Test
Method.

Nociceptive reaction was evaluated by chemical irritation method—writhing test (Charaborty A et al, *Indian J of Pharmacology* 2004; 36(3):148-150). Animals received i.p. 0.25 ml of 0.75% aqueous acetic acid solution: After the injection animals were placed separately in special boxes and observed for 10 minutes. The number of abdominal constrictions was registered. Analgesic activity was manifested by reduction of the number of abdominal constrictions in the 10 minutes period. Test substances were introduced 30 min before the irritating agent. The level of analgesia was expressed as analgesic index calculated as follows:

$$A=(Cc-Ct)/Cc \cdot 100\%, \text{ where}$$

A—Analgesic index
Cc—number of contractions in control group,
Ct—number of contractions in the test group.
The results are presented in Table 4.

TABLE 4

Analgesic effect of test substances in writhing test model; N = 8; Mean ± SEM

| Group | Animals with positive reaction/total number | No. of constrictions | Analgesic index |
|---|---|---|---|
| Control | 8/8 | 22.00 ± 1.60 | — |
| MD100 | 8/8 | 22.10 ± 1.47 | −0.4 |
| ASA50 | 6/8 | 5.75 ± 1.32***$$$ | 7.1 |
| MASA75 | 8/8 | 12.13 ± 0.61**$$ | 4.5 |
| MASA150 | 7/8 | 10.63 ± 1.10**$$ | 5.2 |
| MASA300 | 5/8 | 6.00 ± 1.39***$$$ | 7.3 |

**P < 0.005 vs Control -
***P < 0.0005 vs Control -
$$P < 0.005 vs MD
$$$P < 0.0005 vs MD MASA showed dose dependant positive effect. The best results were observed in ASA50 and MASA300 (P<0.0005) groups, while MD was inactive. The analgesic index for MASA300 group was 7.3 (only 5 animals of 8 had pain reaction).

5.1.2. Evaluation of Analgesic Activity by Mouse Hot Plate Test
Method.

The hot plate test was conducted on 52 mice with body weight 17-26 g as described, in literature (Belyakov V A, Solov'ev I K. *Narcotic analgesics*, Nizhny Novgorod, 2001 (Rus). The hot plate test is used to screen centrally acting analgesics (Osterberg A et al, *J Pharmacol Exper Ther* 1958; 122:59). Aqueous solutions of test substances were introduced p.o. 30 or 60 min. before the testing. The time until the licking of paws was recorded. The criterion of analgesic activity was the delay of response to thermal irritation.
The results are presented in Table 5.

TABLE 5

Response time in mouse hot plate test; N = 8-10; Mean ± SEM

| | Latent period, s | |
|---|---|---|
| Group | At 30 min after introduction of test substance | At 60 min after introduction of test substance |
| Control | 4.5 ± 0.42 | 5.0 ± 0.27 |
| MD100 | 9.5 ± 0.68***&& | 8.3 ± 0.53*** |
| ASA50 | 5.4 ± 0.46 | 9.7 ± 1.05** |
| MASA75 | 5.4 ± 0.38 | 4.6 ± 0.26 |
| MASA150 | 9.5 ± 0.53***&&& | 7.1 ± 0.55** |
| MASA300 | 9.6 ± 1.12**& | 8.6 ± 0.60*** |

**P < 0.005 vs Control -
***P < 0.0005 vs Control -
&P < 0.05 vs ASA (30 min)
&&P < 0.005 vs ASA (30 min) -
&&&P < 0.0005 vs ASA (30 min)

Experimental data indicated that MASA150 and MASA300 as well as MD group manifest significant analgesic effect after 30 and 60 minutes. ASA significantly increased the pain threshold only after 60 minutes indicating a slower onset of effect (Table 5).

5.2. Comparative Evaluation of Antipyretic Activity of Test Substances
5.2.1. Evaluation of the Preventive Antipyretic Activity on Rats by Injection of Pyrogenal
Method.

Experiments were conducted on 48 Wistar rats with body mass 165-182 g by intramuscular injection of pyrogenal (Gamalei State Research Institution, Moscow, Russia) in 100 µg dose (Shwarz G Y, Syubaev R D, *Vedomosti NCEG lekarstvennyh sredstv MZ RF* 2000; 1:44-50 (Rus). Test substances were given p.o. one hour before the pyrogenal injection. Rectal temperature was measured by electric thermometer TERMO before injection of pyrogenal (baseline) and for 3 hours after injection. The antipyretic activity was evaluated by the reduction of hyperthermic reaction 2 hours after injection of pyrogenal that correlated well with the published data (10) about the peak of reaction (Table 6). Ambient temperature was kept at 20-21° C.

As follows from the data, the body temperature of the control group animals gradually increased, reached maximum in 2 hours and continued to be over norm for another hour.

TABLE 6

Changes of rat rectal temperature of control group under the influence of pyrogenal; N = 8; Mean ± SEM

| | | Rectal temperature (° C.) | | | |
|---|---|---|---|---|---|
| Group | Baseline (° C.) | after 30 min | after 60 min | after 120 min | after 180 min |
| Control | 36.16 ± 0.16 | 36.25 ± 0.21 | 36.75 ± 0.12## | 36.90 ± 0.10### | 36.70 ± 0.17# |

P < 0.05 vs baseline -
P < 0.005 vs baseline -
P < 0.0005 vs baseline

The test substances did not substantially influence the normal body temperature of animals but substantially reduced pyrogenal induced hyperthermia (Table 7).

TABLE 7

Influence of test substances on hyperthermia, induced by intramuscular injection of pyrogenal; N = 8; Mean ± SEM

| Group | Baseline rectal temperature (° C.) | Rectal temperature (° C.) 120 minutes after injection |
|---|---|---|
| Control | 36.2 ± 0.12 | 36.9 ± 0.16## |
| MD100 | 35.9 ± 0.18 | 36.2 ± 0.16* |
| ASA50 | 35.8 ± 0.17 | 35.6 ± 0.19***$ |
| MASA75 | 36.1 ± 0.18 | 36.3 ± 0.20* |
| MASA150 | 35.8 ± 0.15 | 36 ± 0.21** |
| MASA300 | 35.9 ± 0.14 | 35.8 ± 0.16***$ |

*P < 0.05 vs Control -
**P < 0.005 vs Control -
***P < 0.0005 vs Control
P < 0.005 vs baseline -
$P < 0.05 vs MD In the hyperthermia model the increase in body temperature induced by injection of pyrogenal was completely prevented in ASA50 and MASA300 groups (Table 7). In MD100, MASA75 and MASA150 groups the antipyretic effect was less pronounced.

5.2.2. Evaluation of the Preventive Antipyretic Activity on Rats by Injection of Pyrogenal (Curative Mode)
Method.

The antipyretic effect of test substances in therapeutic (curative) mode was investigated on 48 rats with body mass 182-205 g, with hyperthermia induction by injecting pyrogenal in dose 100 μg (Shwarz G Y, Syubaev R D, Vedomosti NCEG lekarstvennyh sredstv MZ RF 2000; 1:44-50 (Rus). Test substances were given p.o. 2 hours after injection of pyrogenal immediately after the recording of elevated body temperature. Rectal temperature was measured by electric thermometer TERMO before the i.m. injection of pyrogenal (baseline temperature), at the peak of hyperthermia (pyrogenal control) and 30 min. after treatment with test substance, i.e., 2½ hours after the injection of pyrogenal. Ambient temperature in laboratory was kept at 20-22° C. The results are presented in Table 8.

TABLE 8

Influence of test substances on hyperthermia, induced by intramuscular injection of pyrogenal (curative mode); N = 8; Mean ± SEM

| Group | Baseline rectal temperature (° C.) | Rectal temperature (° C.) after injection of pyrogenal (pyrogenal control) | Rectal temperature (° C.) at 30 minutes after treatment |
|---|---|---|---|
| Control | 36.10 ± 0.15 | 36.90 ± 0.20## | 37.00 ± 0.18## |
| MD100 | 36.41 ± 0.14 | 37.06 ± 0.13## | 37.10 ± 0.14## |
| ASA50 | 36.39 ± 0.13 | 37.04 ± 0.25# | 36.51 ± 0.15*$ |
| MASA75 | 36.23 ± 0.12 | 37.01 ± 0.11## | 36.90 ± 0.07## |
| MASA150 | 36.25 ± 0.20 | 36.96 ± 0.15# | 36.75 ± 0.09#$ |
| MASA300 | 36.11 ± 0.14 | 36.76 ± 0.11## | 36.40 ± 0.11*$$% |

*P < 0.05 vs Control -
P < 0.05 vs baseline -
P < 0.005 vs baseline
%P < 0.05 vs pyrogenal control -
$P < 0.05 vs MD -
$$P < 0.005 vs MD Pyrogenal caused significant and similar increase of body temperature to all animals used in the experiment (comp. pyrogenal control vs. baseline, Table 8). The treatment with test substances, except MD, caused the lowering of body temperature vs. baseline and pyrogenal control. The comparatively higher hypothermia was observed in MASA300 and ASA50 groups where the lowering of body temperature was significant vs control and MD100. It should be noted that in MASA300 group, contrary to ASA50, the lowering of body temperature was significant also against the pyrogenal control. It indicated considerable and rapid antipyretic effect of MASA that might be valuable in clinic.

5.3. Comparative Evaluation of Anti-Inflammatory Activity of Test Substances
5.3.1. The Investigation on the Acute Inflammatory Oedema Model
Method.

Experiments were conducted using carrageneen test (Winter C et al, *Proc Soc Exptl Biol and Med* 1962; III(3):544-547. Wei Jia et al, *Journal of Ethnopharmacology* 2003(89):139-141; Sutharson Lingadurai et al, *African Journal of traditional, complementary and alternative medicines*, 2007, 4(4): 411-416) on 42 rats with body mass of 226-274 g. Single injection of carrageneen (Sigma) solution (1%) in saline (0.1 ml) was introduced in rat hind leg paw. Test substances were introduced p.o. (through catheter into rat stomach) 30 min. after the injection of carrageneen. The volume of paw was measured by oncometer at baseline and 4 hours after the injection of carrageneen.

The percentage of prevention (inhibition of oedema) was calculated according to formula:

$P(\%) = (1 - Vo/Vc) \times 100$, where

P—Prevention in % (inhibition of oedema)
Vo—difference between the paw volume at baseline and at experimental conditions;
Vc—analogical difference in control group.
The results are presented in Table 9.

TABLE 9

Anti-exudative activity of test substances in carrageneen inflammation model; N = 7, Mean ± SEM

| Group | Volume of paw (ml) at baseline | Volume of paw (ml) after injection of carrageneen ml | Index, % |
|---|---|---|---|
| Control | 1.6 ± 0.30 | 2.70 ± 0.13 | 0 |
| MD100 | 1.5 ± 0.34 | 2.13 ± 0.12* | 43 |
| ASA100 | 1.6 ± 0.32 | 1.97 ± 0.10** | 66 |
| MASA75 | 1.6 ± 0.44 | 2.51 ± 0.11 | 18 |
| MASA150 | 1.6 ± 0.31 | 1.54 ± 0.15***$& | 93 |
| MASA300 | 1.7 ± 0.25 | 1.79 ± 0.15** | 91 |

*P < 0.05 vs Control -
**P < 0.005 vs Control -
***P < 0.0005 vs Control -
&P < 0.05 vs ASA100 -
$P < 0.05 vs MD In the acute inflammatory oedema model the volume of affected extremity in control group increased approximately 1.6 times. The most pronounced effect on the inflammatory process was observed in MASA150 group, where the preventive index was 93% vs the control group. In the MASA300 group the activity was slightly less—the oedema was reduced by 91%. Reduction of oedema was also observed in MD100 and ASA50 groups.

5.3.2. Investigation of Anti-Inflammatory Activity of Test Substances Against Carrageneen Oedema in Preventive Mode
Method.

The carrageneen oedema was investigated by established method (Okunevich I V, Ryzhenkov V E, *Patol Fiziol Eksp Ter*, 2002(2):24-7 (Rus) on 42 rats with body mass of 178-220 g: The test substances were introduced p.o. during a 5 day period. On Day 6 immediately after the introduction of test substances rats were given a 0.1 ml injection of 1% carrageneen solution in hind paw. The volume of paw was measured at baseline and 4 hours after the injection of carrageneen. The prevention index was calculated as indicated in previous section. The preventive introduction of test substances for 6 times caused a reduction of oedema compared to untreated animals (Table 10).

TABLE 10

Preventive anti-exudative action of test substances against carrageneen oedema; N = 7, Mean ± SEM

| Group | Volume of paw (ml) at baseline | Volume of paw (ml) after injection of carrageneen ml | Reduction in % |
|---|---|---|---|
| Control | 1.43 ± 0.12 | 1.93 ± 0.11 | 0 |
| MD100 | 1.33 ± 0.09 | 1.66 ± 0.10 | 34 |
| ASA50 | 1.40 ± 0.06 | 1.55 ± 0.04* | 70 |
| MASA150 | 1.37 ± 0.11 | 1.40 ± 0.09**$ | 94 |
| MASA300 | 1.34 ± 0.07 | 1.41 ± 0.04**$ | 86 |

*$P < 0.05$ vs Control -
**$P < 0.005$ vs Control -
$$P < 0.05$ vs MD

In the MASA150 and MASA300 groups a significant preventive activity (94%) was observed, that was higher than that in MD 100 (34%) and ASA50 (70%) groups in this inflammatory model (Table 10).

To evaluate the intensity of the inflammation process the CRP levels were determined by standard method on analyzer «INTEGRA 400+» at the end of experiment (5 hours after injection of carrageneen).

Results of determination of CRP in blood are presented in Table 11.

TABLE 11

The levels of CRP in rat blood at the carrageneen inflammation model for rats; N = 7, Mean ± SEM

| Group | CRP mg/l | CRP increase % |
|---|---|---|
| Control | 0.17 ± 0.015 | 0 |
| Carrageneen control | 0.23 ± 0.016** | 100 |
| MD100 | 0.22 ± 0.014* | 83 |
| ASA100 | 0.20 ± 0.018 | 50 |
| MASA150 | 0.19 ± 0.009#$ | 33 |
| MASA300 | 0.21 ± 0.014* | 67 |

*$P < 0.05$ vs Control -
**$P < 0.005$ vs Control -
$P < 0.05$ vs Carrageneen control
$$P < 0.05$ vs MD As follows from the data carrageneen caused the increase of CRP in rat blood. In ASA100 group the CRP level increase was reduced by 50% (Table 11). Unexpectedly in MASA150 group the CRC level increase was significantly less pronounced (only 33% to control). It supports the opinion that MASA can have positive effects on inflammatory process in clinic.

Example 6

Investigation of Antirheumatic Activity of MASA in Comparison with ASA and MD

Clinical evidence shows that patients with rheumatoid arthritis (RA) are predisposed to atherosclerosis and cardiovascular disease (Nasonov E L, *Vestn Ross Akad Nauk* 2003 (7):6-10). Patients with prolonged RA have more atherosclerosis than patients of the same age with more recent disease onset. Systemic inflammation may amplify the age-related risk of cardiovascular disease (Del Rincon I et al, *Atherosclerosis* 2007; 196(2):354-360).

Rheumatoid arthritis holds the top position among the rheumatoid conditions. The most adequate experimental animal model for human rheumatoid arthritis is the model of adjuvant arthritis, induced by injection of Freund's adjuvant in rat hind foot pads. It is widely used in screening of antiarthritic agents (Wei Jia et al, *Journal of Ethnopharmacology* 2003(89):139-141; Sutharson Lingadurai et al, *African Journal of traditional, complementary and alternative medicines*, 2007, 4(4):411-416).

Methods.

Our experiments were scheduled to test the influence of MASA on the progress of adjuvant arthritis in comparison with MD and ASA. Experiments were conducted on Wistar rats with starting body mass of 153-185 g. Rats were kept in climatized rooms at 22±1° C., relative humidity 60±5% and 12/12-hour light/darkness cycle. Each standard cage housed 7 rats with unlimited access to drinking water and granulated standard feed. All experiments were carried out in accordance with the European Community Council's Directive of 24 Nov. 1986 (86/609/EEC) relative to experimental animal care. All efforts were made to minimize animal suffering and to reduce the number of animals used.

A modified standard procedure for inducting and evaluating the progress of chronic adjuvant arthritis was used (Bellavite P, Ortolani R, Conforti A, *Immunology and Homeopathy*. 3. *Experimental Studies on Animal Models, Advance Access Publication* 2.05, 2006, 171-186). Rats were injected into the hind foot pad 0.1 ml and intraperitonealy with 0.05 ml of complete Freund's adjuvant solution.

The solutions of test substances were prepared ex tempore. ASA was used as 0.1% and 1%, MD as 1% and MASA as 0.25%, 1% and 2% aqueous solution. Test solutions were introduced to animal p.o. by catheter into the stomach.

The following animal groups were formed (N=7):

| GROUP | TREATMENT |
|---|---|
| Group 1 | intact animals, used as controls (Control); |
| Group 2 | animals with induced adjuvant arthritis (AdA); |
| Group 3 | animals receiving ASA in dose 10 mg/kg daily for 28 days after the induction of adjuvant arthritis (ASA10); |
| Group 4 | animals receiving ASA in dose 100 mg/kg daily for 28 days after the induction of adjuvant arthritis (ASA100); |
| Group 5 | animals receiving MD in dose 100 mg/kg daily for 28 days after the induction of adjuvant arthritis (MD100); |
| Group 6 | animals receiving MASA in dose 25 mg/kg daily for 28 days after the induction of adjuvant arthritis (MASA25); |
| Group 7 | animals receiving MASA in dose 100 mg/kg daily for 28 days after the induction of adjuvant arthritis (MASA100); |
| Group 8 | animals receiving MASA in dose 200 mg/kg daily for 28 days after the induction of adjuvant arthritis (MASA200); |

Animals of Control group and animals of AdA group instead of test substances received water p.o. on the same schedule as test groups.

Statistics.

Data were analyzed by Microsoft Excel 2007 software and results expressed as Mean±SEM. Mean results of different groups were compared using single-factor analysis according to ANOVA with repeated comparison (Tukey's test). $P<0.05$ was considered as significant.

Results.

Dynamics of clinical manifestation of arthritis was investigated on Day 14 and Day 28. The effects of test substances were evaluated using the following criteria:

1. Evaluation of local manifestation of arthritis—volume of paw and circuit of ankle joint.
2. Evaluation of blood count (WBC).
3. Evaluation of biochemical tests (CRP).
4. Evaluation of immunological indices (levels of CIC).

The oedema, i.e. the volume of hind paw was measured by oncometer. The percentage of prevention (inhibition of oedema) was calculated according to formula:

$$P(\%) = (Vc - Vt)/Vc \times 100, \text{ where}$$

Vc—paw volume in control group
Vt—paw volume in test group
P—Prevention in % (inhibition of oedema).

Hematological indices were determined by standard methods on hematological analyzer « PENTRA 120 », CRP was determined on « INTEGRA 400+ ». Levels of CIC in blood serum were determined spectrometrically, using ethylene glycol.

After injection of Freund's adjuvant all animals of test groups developed chronical inflammation, rats were weary, aggressive on handling, tousled. However the feeding habits in all groups were not different from controls. The increase of body mass in all groups was not substantially different from the control group.

In Tables 12 and 13 the data on local manifestation of arthritis are presented: the volume of paw (characterizing oedema of soft tissue) and circuit/volume of ankle joint (characterizing arthritic type organic damages of joint tissues) on Day 14 and Day 28.

TABLE 12

Effects on paw volume (ml) by test substances on Day 14 and Day 28 after the injection of Freund's adjuvant; N = 7; Mean ± SEM

| Group | Paw volume on Day 14 | | Paw volume on Day 28 | |
|---|---|---|---|---|
| | ml | Prevention % | ml | Prevention % |
| Control | 1.03 ± 0.12### | — | 1.08 ± 0.17### | — |
| AdA | 2.42 ± 0.17 | 0 | 2.23 ± 0.24 | 0 |
| ASA 10 | 2.53 ± 0.10 | −7 | 2.08 ± 0.12 | 7 |
| ASA100 | 2.35 ± 0.14 | 3 | 1.52 ± 0.07# | 32 |
| MD100 | 2.60 ± 0.21 | −7 | 1.93 ± 0.13 | 13 |
| MASA25 | 2.20 ± 0.21 | 9 | 1.32 ± 0.12#&&$ | 41 |
| MASA100 | 2.07 ± 0.17& | 15 | 1.22 ± 0.08#&&@$ | 45 |
| MASA200 | 2.13 ± 0.11& | 12 | 1.7 ± 0.09#&@ | 24 |

P < 0.05 vs AdA -
P < 0.0005 vs AdA -
&P < 0.05 vs ASA10 -
&&P < 0.005 vs ASA10
&&&P < 0.0005 vs ASA10 -
@P < 0.05 vs ASA100 -
$P < 0.05 vs MD

As follows from data of Table 12 on Day 14 all animals of test groups developed pronounced oedema of soft tissues. Treatment during 14 days relatively little influenced the development of oedema. However, animals in groups MASA100 and MASA200 had significantly less pronounced oedema than animals in ASA10 group. MD and ASA10 on Day 14 did not prevent the development of oedema, but had even higher volumes as compared to AdA group (negative protection −7%). MASA in all doses and ASA100 on Day 28 significantly protected from development of oedema (protection %, respectively, 41, 45, 24 and 32%). It should be noted that MASA100 displayed significantly better protection than ASA10, ASA 100 and MD.

TABLE 13

Effect of test substances on changes in rat ankle joints on Day 14 and Day 28 after injection of Freund's adjuvant. N = 7; Mean ± SEM

| Group | Dimensions of ankle joint on Day 14, mm | Dimensions of ankle joint on Day 28, mm |
|---|---|---|
| Control | 5.6 ± 0.09## | 5.8 ± 0.12## |
| AdA | 7.2 ± 0.14 | 7.3 ± 0.16 |
| ASA10 | 7.2 ± 0.12 | 6.8 ± 0.14# |
| ASA100 | 6.9 ± 0.15 | 7.1 ± 0.16 |
| MD100 | 7.0 ± 0.13 | 7.0 ± 0.13 |
| MASA25 | 7.0 ± 0.14 | 6.7 ± 0.15# |
| MASA100 | 7.0 ± 0.13 | 6.6 ± 0.16#@$ |
| MASA200 | 6.8 ± 0.10#& | 6.9 ± 0.11 |

P < 0.05 vs AdA -
P < 0.005 vs AdA -
&P < 0.05 vs ASA10 -
@P < 0.05 vs ASA100
$P < 0.05 vs MD

Analysis of ankle joint data (Table 13) shows that on Day 14 only MASA200 had significantly protected against progressing of arthritic damages. On Day 28 significant protection was shown by MASA25, MASA100 and ASA100. Comparatively best protection in this experimental setting was displayed by MASA100. We have established that on Day 28 the level of oedema (Table 12) and arthritic changes in ankle joint (Table 13) were diminished. MASA100 was significantly more effective than ASA or MD. The evaluation of WBC showed increase (leucocytosis) under the influence of Freund's adjuvant (Table 14). Leucocytosis is a characteristic feature of inflammation process.

TABLE 14

Changes of WBC in rat blood under the influence of test substances on Day 14 and Day 28 after injection of Freund's adjuvant. N = 7; Mean ± SEM

| | Leucocytes $10^3/mm^3$ | |
|---|---|---|
| Group | Day 14 | Day 28 |
| Control | 15.17 ± 0.76## | 16.50 ± 0.52## |
| AdA | 21.48 ± 1.47** | 20.32 ± 0.90** |
| ASA10 | 15.83 ± 1.23# | 16.68 ± 1.22# |
| ASA10 | 17.07 ± 1.43 | 16.91 ± 1.17# |
| MD100 | 14.42 ± 1.41# | 15.55 ± 1.26# |
| MASA25 | 14.72 ± 1.63# | 16.77 ± 1.78 |
| MASA100 | 14.13 ± 0.53## | 15.52 ± 0.57## |
| MASA200 | 15.42 ± 1.40# | 14.35 ± 0.84## |

**P < 0.005 vs Control -
P < 0.05 vs AdA -
P < 0.005 vs AdA

Use of test substances caused lowering of WBC compared to AdA group indicating the anti-inflammation activity. Although there was no statistically significant difference between the effects of test substances on leucocyte level increase, on Day 14 the comparatively higher activity was displayed by MASA100, but on Day 28—by MASA200 (Table 14). For evaluation of the development of inflammation process the levels of CRP on Day 14 and Day 28 were determined. The levels of CRP are known to increase during inflammatory process.

TABLE 15

Changes of CRP levels in rat blood under the influence of test substances on Day 14 and Day 28 after injection of Freund's adjuvant. N = 7; Mean ± SEM

| Group | CRP, mg/l | |
|---|---|---|
| | Day 14 | Day 28 |
| Control | 0.19 ± 0.01### | 0.16 ± 0.02## |
| AdA | 0.30 ± 0.02*** | 0.24 ± 0.02** |
| ASA10 | 0.26 ± 0.01** | 0.19 ± 0.01# |
| ASA100 | 0.29 ± 0.01*** | 0.18 ± 0.02# |
| MD100 | 0.26 ± 0.02** | 0.17 ± 0.02# |
| MASA25 | 0.29 ± 0.02** | 0.15 ± 0.02##& |
| MASA100 | 0.29 ± 0.02** | 0.16 ± 0.01##& |
| MASA200 | 0.25 ± 0.01*#@ | 0.19 ± 0.01# |

*P < 0.05 vs Control -
**P < 0.005 vs Control -
***P < 0.0005 vs Control
P < 0.05 vs AdA -
P < 0.005 vs AdA -
P < 0.0005 vs AdA -
&P < 0.05 vs ASA10
@P < 0.05 vs ASA100

As follows from data in Table 15, on Day 14 all test groups showed increased levels of CRP as indication of inflammatory process. In our experimental settings only MASA200 displayed significant protection from increase of CRP on Day 14. It should be noted that MASA200 on Day 14 had substantially better effect than MASA100. On Day 28 the significantly better protection was displayed by MASA25 and MASA100 that were better than ASA10 (Table 15).

CIC levels were determined by standard spectrophotometric method (Baranovskii P V, Rudyk B I, *Laboratornoe delo* 1982; 12:35-39 (Rus). Immunological factors were investigated in dynamics on Day 14 and Day 28. Changes in CIC levels are displayed in Table 16.

TABLE 16

Quantity (units) of CIC on Day 14 and Day 28 after injection of Freund's adjuvant. N = 7; Mean ± SEM

| Group | CIC units, Day 14 | CIC units, Day 28 |
|---|---|---|
| Control | 9.4 ± 1.05## | 7.8 ± 0.49## |
| AdA | 17.4 ± 1.29** | 13.4 ± 1.25** |
| ASA10 | 10.8 ± 0.74## | 8.2 ± 0.53# |
| ASA100 | 15.0 ± 1.23* | 14.4 ± 1.66* |
| MD100 | 11.8 ± 2.22 | 8.6 ± 0.93# |
| MASA25 | 12.6 ± 0.68# | 11.8 ± 1.53 |
| MASA100 | 20.8 ± 2.99* | 5.8 ± 0.74##&@@$ |
| MASA200 | 21.6 ± 3.26* | 6.2 ± 1.02##@ |

*P < 0.05 vs Control -
**P < 0.005 vs Control -
P < 0.05 vs AdA -
P < 0.005 vs AdA
$P < 0.05 vs MD -
&P > 0.05 vs ASA10 -
@P < 0.05 vs ASA100 -
@@P < 0.005 vs ASA100

On Day 14 and Day 28 the CIC levels in test groups were higher than in Control group. On Day 14 the CIC levels were lower than in AdA group only in ASA10 and MASA25 group. CIC on Day 28 in groups receiving test substances were close to controls, except than ASA100 group.

During the experiment an increase in CIC levels on Day 14 was observed in ASA100 and MASA100 and MASA200 groups. On Day 28 the CIC levels in MASA100 and MASA200 groups the CIC levels had normalised. The increase of CIC levels in blood serum can be observed in various pathological immunity conditions. Substantial increase of CIC is observed in inflammatory processes, including systemic conditions, with CIC levels indicating the intensity of the pathological process (Bier O et al, *Fundamentals of immunology*, New York, Heidelberg, Berlin, p. 442). Prolonged treatment with MASA in various doses lowered the CIC levels to norm. At sufficiently active immunity the main part of CIC is removed by Kupfer's cells and lowering of CIC levels is perceived as positive effect. The fact that use of MASA in MASA100 and MASA200 groups displayed normalising effect on CIC levels on Day 28 indicated that prolonged use of MASA in various doses might be clinically more promising in treatment of arthritis than elevated doses of ASA.

Example 7

Investigation of Anti-Hyperlipidemic Properties

Atherosclerosis is a multifactoral process (Berliner J A et al, *Circulation* 1995; 91:2488-2495) with increasing clinical impact along with increasing coronary heart disease symptoms. A substantial role in the atherosclerotic process is played by inflammation and organism's response to it (Ross R, *Am Heart J* 1999; 138;S419-S420). Clinical observations indicate that anti-inflammation therapy reduces the manifestations of atherosclerosis (Stoller D K et al, *J Surg Res* 1993; 54:7-11). Experimental data confirm the considerable correlation of anti-inflammation activity with hypolipidemic activity at least among COX-1 inhibitors (Kourounakis A P et al, *Exper Mol Pathol* 2002; 73:135-138). We compared the hypolipidemic activity of ASA and MASA in equivalent doses.

7.1. Comparative Effects of Test Substances on Lipid Levels in Rat Acute Hyperlipidemia Model Methods.

Male Wistar rats with body mass of 250-270 g were used. Animals were held in groups of 6-8 in climatized rooms at 22±1° C., relative humidity 60±5%, and 12/12-hour light/dark cycle with free access to water and feed. Acute experimental hyperlipidemia/hypercholesterolemia was induced by Triton WR1339 (TR) as described by Kourounakis A P et al, *Exper Mol Pathol* 2002; 73:135-138). Rats after overnight fasting were treated i.p. by TR dissolved in isotonic saline in 250 mg/kg dose. The solution of test substances or water was introduced to control and TR group animals p.o. one hour before and 20 hours after the introduction of TR as described below.

Blood for biochemical analysis was collected on the next day (24 hours after the injection of TR) by heart punction under ether narcosis. Serum was separated by centrifugation and analyzed for total cholesterol, HDL, LDL and TG levels by commercial kits.

Three series of experiments were conducted.

Statistics.

Data were analyzed by Microsoft Excel software and results expressed as mean+/−mean standard error of mean. Mean results of different groups were compared using single-factor analysis according to ANOVA and t-Student's test. $P<0.05$ was considered as significant.

I Series—ASA, MD and MASA Compared

| GROUP | TREATMENT | Number of animals |
|---|---|---|
| Control | | 6 |
| TR | TR 250 mg/kg | 8 |
| ASA45 | TR 250 mg/kg + ASA 45 mg/mg | 6 |
| ASA90 | TR 250 mg/kg + ASA 90 mg/mg | 8 |
| MD150 | TR 250 mg/kg + MD 150 mg/kg | 8 |
| MASA75 | TR 250 mg/kg + MASA 75 mg/kg | 6 |
| MASA150 | TR 250 mg/kg + MASA 150 mg/kg | 8 |
| MASA300 | TR 250 mg/kg + MASA 300 mg/kg | 8 |

Results.

Rats that received TR developed pronounced hypercholesterolemia and hyperlipidemia with total cholesterol, LDL and TG levels significantly different from those of control group (total C increase 6-7 times, TG 30—and more, see Table 17). ASA therapy, especially in dose 90 mg/kg, limited the increase of total C, LDL and TG, but did not significantly change the level of HDL. MD in our experimental setting did not significantly protect from the changes in lipid levels caused by TR. Treatment with MASA caused dose dependant protection from TR-induced hyperlipidemia/hypercholesterolemia. MASA in dose 75 mg/kg does not differ from ASA45, but MASA150 is considerably more efficient than ASA45 and MD 150 in protecting from TR effects. MASA300 considerably better than ASA45 and ASA90 lowered the levels of total C, LDL and TG. It indicates that MASA can be useful in preventing and/or treating hypercholesterolemic and hyperlipidemic conditions and considering its anti-inflammation activity can be useful in preventing and/or treating of atherosclerosis and other conditions advanced by disturbances in lipid metabolism and inflammation.

| GROUP | TREATMENT | Number of animals |
|---|---|---|
| Control | | 6 |
| TR | TR 250 mg/kg | 8 |
| ASA45 | TR 250 mg/kg + ASA 45 mg/mg | 6 |
| MASA | TR 250 mg/kg + MASA 150 mg/kg | 6 |
| NA | TR 250 mg/kg + NA 50 mg/kg | 7 |
| ASA + NA | TR 250 mg/kg + ASA 45 mg/kg + NA 50 mg/mg | 7 |
| MASA + NA | TR 250 mg/kg + MASA 150 mg/kg + NA 50 mg/kg | 7 |

Results.

In our experimental setting NA provided significant protection against changes in lipid (C, LDL and TG) levels induced by TR (See Table 18). The combination of ASA and NA did not significantly change the effect of NA on lipid levels. Surprisingly the combination of MASA and NA considerably enhanced the effect of NA50 and surpassed the protective effect of MASA on TG levels increase caused by TR (Table 18). The combined use of MASA and NA was also

TABLE 17

Comparative effects of MD, ASA and MASA on lipid levels in rat hyperlipidemia model; n = 6-8; Mean ± SEM

| Group | C mg/dl | HDL mg/dl | LDL mg/dl | TG mg/dl |
|---|---|---|---|---|
| Control | 80.7 ± 4.7*** | 56.5 ± 2.8 | 21.1 ± 2.6*** | 44.0 ± 6.9*** |
| TR | 453.6 ± 40.0 | 60.3 ± 9.6 | 386.0 ± 36.5 | 1399 ± 129.7 |
| ASA45 | 381.0 ± 30.3 | 62.8 ± 10.9 | 307.4 ± 37.8 | 973 ± 82.7* |
| ASA90 | 288.1 ± 23.5* | 60.0 ± 7.4 | 219.1 ± 23.9* | 791 ± 73.9** |
| MD150 | 345.6 ± 34.1 | 63.8 ± 9.3 | 273.9 ± 31.6* | 1022 ± 80.7* |
| MASA75 | 341.9 ± 16.3* | 68.1 ± 8.7 | 270.1 ± 12.8* | 861 ± 105.7* |
| MASA150 | 249.6 ± 22.2**$& | 58.2 ± 8.1 | 182.4 ± 19.6**$& | 668 ± 104.4**$& |
| MASA300 | 219.0 ± 16.7**$#& | 56.3 ± 8.6 | 158.6 ± 19.4**$#& | 548 ± 73.2***&$# |

*P < 0.05 vs TR -
**P < 0.005 vs TR -
***P < 0.0005 vs TR -
$P < 0.05 vs ASA45
P < 0.05 vs ASA90 -
&P < 0.05 vs MD150

II Series—ASA, MASA, NA and Combinations ASA+NA, MASA+NA Compared significantly more efficient than normalizing effect of ASA45+NA50 on LDL and TG levels.

TABLE 18

The effects of MD, ASA and MASA, separately and in combination, on lipid levels in rat hyperlipidemia model; n = 6-8; Mean ± SEM

| Group | C mg/dl | HDL mg/dl | LDL mg/dl | TG mg/dl |
|---|---|---|---|---|
| Control | 80.7 ± 4.7*** | 56.5 ± 2.8 | 21.1 ± 2.6*** | 44 ± 6.9*** |
| TR | | 60.3 ± 9.6 | 386.0 ± 36.5 | 1399 ± 129.7 |
| ASA45 | 381.0 ± 30.3 | 62.8 ± 10.9 | 307.4 ± 37.8 | 973 ± 82.7* |
| MASA150 | 249.6 ± 22.2**$ | 58.2 ± 8.1 | 182.4 ± 19.6**$ | 668 ± 70.9**$ |
| NA50 | 327.5 ± 38.4* | 66.5 ± 14.6 | 246.3 ± 32.5* | 591 ± 43.3** |
| ASA45 + NA50 | 316.0 ± 43.1* | 57.9 ± 14.3 | 251.2 ± 33.8* | 618 ± 42.8** |
| MASA150 + NA50 | 226.3 ± 24.9**#$ | 63.1 ± 10.2 | 163.2 ± 19.3**$#% | 468 ± 34.7**$#%@ |

*P < 0.05 vs TR -
**<0.005 vs TR -
***P < 0.0005 vs TR -
$P < 0.05 vs ASA45
@P < 0.05 vs MASA150 -
P < 0.05 vs NA50 -
%P < 0.05 vs ASA45 + NA50

III Series—SI, MD, MASA and Combinations SI+MD, SI+MASA Compared

| GROUP | TREATMENT | Number of animals |
|---|---|---|
| Control | | 6 |
| TR | TR 250 mg/kg | 8 |
| SI | TR 250 mg/kg + SI 5 mg/kg | 7 |
| MD | TR 250 mg/kg + MD 150 mg/kg | 6 |
| MASA | TR 250 mg/kg + MASA 150 mg/kg | 6 |
| SI + MD | TR 250 mg/kg + SI 5 mg/kg + MD 150 mg/kg | 7 |
| SI + MASA | TR 250 mg/kg + SI 5 mg/kg + MASA 150 mg/kg | 7 |

Results.

In our experimental setting SI in 5 mg/kg dose provided significant protection against changes in lipid (C, LDL and TG) levels induced by TR (see Table 19). The combination of SI with the test substances increased the normalizing effect on lipid levels. MASA in combination with SI was significantly more efficient than MD+SI in counteracting the increase of LDL and TG levels caused by TR (Table 19). Combination of MD with statins has been proposed in WO2006099244 without any data. Combined use of statins and ASA requires special pharmaceutical composition, since the substances are pharmacologically and chemically incompatible (U.S. Pat. No. 6,235,311), therefore no synergy is possible.

TABLE 19

The effects of MD, MASA and SI, separately and in combination, on lipid levels in rat hyperlipidemia model; n = 6-8; Mean ± SEM

| Group | C mg/dl | HDL mg/dl | LDL mg/dl | TG mg/dl |
|---|---|---|---|---|
| Control | 80.7 ± 4.7*** | 56.5 ± 2.8 | 21.1 ± 2.6*** | 44 ± 6.9*** |
| TR | 453.6 ± 40.0 | 60.3 ± 9.6 | 386.0 ± 36.5 | 1399 ± 129.7 |
| SI | 321.3 ± 32.3* | 53.7 ± 12.4 | 259.3 ± 30.1* | 826 ± 44.1** |
| MD | 345.6 ± 34.1 | 63.8 ± 9.3 | 273.9 ± 31.6* | 1022 ± 80.7* |
| MASA | 249.6 ± 22.2**& | 58.2 ± 8.1 | 182.4 ± 19.6**& | 668 ± 70.9***& |
| SI + MD | 281.5 ± 31.2**& | 59.5 ± 14.9 | 217.1 ± 26.2* | 690 ± 32.6***&$ |
| SI + MASA | 230.7 ± 28.6***&$ | 62.8 ± 14.6 | 153.4 ± 28.0***&$# | 512 ± 40.2***&$# |

*P < 0.05 vs TR -
**<0.005 vs TR -
***P < 0.0005 vs TR -
&P < 0.05 vs MD -
$P < 0.05 vs SI -
P < 0.05 vs MD + SI

Summary.

The results indicate the potential of MASA in preventing and/or treating of hypercholesterolemia and hyperlipidemia. Considering the anti-inflammatory activity of MASA it can be more efficient than ASA or MD in preventing and/or treating of atherosclerosis and other conditions advanced by inflammation. The combined use of MASA and NA enhances the positive effects of separate substances on experimentally increased lipid levels better than ASA plus NA. MASA in combination with SI was not only more efficient than SI alone, but was also significantly more efficient than MD+SI in counteracting the increase of LDL and TG levels caused by TR.

7.2. Influence of NA and MASA, Separately and in Combination, on Lipid Levels in Rat Chronic Hyperlipidemia Model Methods.

Male Wistar rats were used. Animals were held in climatized rooms 22±1° C. with relative humidity 60±5%, and 12/12-hour light/dark cycle with free access to water and feed. Initial weight of animals was 220-240 g. Experimental chronical (subchronical) hyperlipidemia/hypercholesterolemia was induced by TR using the method described by Levine and Saltzman (Levine S, Saltzman A, *J Pharmacol Toxicol Meth* 2007; 55:224-226). Animals received 250 mg/kg of TR solution via tail vein three times a week for 3 weeks. Solutions of test substances or water for Control and TR group was introduced p.o. once a day one hour before injection of TR solution or taking a blood sample according to the following scheme:

| GROUP | TREATMENT | Number of animals |
|---|---|---|
| Control | | 10 |
| TR | TR 250 mg/kg | 14 |
| TR + NA | TR 250 mg/kg + NA 50 mg/kg/d | 14 |
| TR + MASA | Triton 250 mg/kg + 150 mg/kg/d | 14 |
| TR + NA + MASA | Triton 250 mg/kg + NA 50 mg/kg + MASA 150 mg/kg/d | 14 |

Blood for biochemical analyses was obtained after 1, 2 and 3 weeks (on the next day after the TR injection) by cardiac punction under ether narcosis. Serum was separated by centrifugation and analyzed for total C, HDL, LDL and TG levels by commercial kits.

Statistics.

Data were analyzed by Microsoft Excel software and results expressed as mean+/−mean standard deviation. Mean results of different groups were compared using single-factor analysis according to ANOVA and t-Student's test. P<0.05 was considered as significant.

Results.

Repeated injections of TR developed pronounced and stable hypercholesterolemia and hyperlipidemia, characterized by significant increase of total C, LDL and TG levels compared to Control (total C increased 6-7 times, TG-30 and more, see Table 21). NA therapy, especially significantly in the first week, limited the increase of total C, LDL and TG, but significantly increased the HDL levels in 2 and 3 week only. MASA almost equally as NA lowered total C and LDL levels and increased HDL levels, but less than NA prevented from the increase of TG, caused by TR (see Table 20). Unexpectedly the combined use of NA+MASA after 3 weeks substantially better than NA or MASA alone lowered total C, LDL and TG levels and increased HDL levels. Thus the combination NA+MASA is expected to be useful for preventing and/or treating hypercholesterolemia and hyperlipidemia.

TABLE 20

Influence of NA and MASA, separately and in combination, on lipid levels in rat hyperlipidemia model; n = 9-14; Mean ± SEM

| | Total C after 1, 2 and 3 weeks, mg/dl | | |
|---|---|---|---|
| Group | C1 | C2 | C3 |
| Control | 77.6 ± 4.9# | 75.1 ± 5.1# | 72.7 ± 2.5# |
| TR | 487.6 ± 25.4 | 501 ± 16.7 | 513 ± 41.1 |
| TR + NA | 345 ± 15.7* | 401.1 ± 25.1** | 405.5 ± 25.9* |
| TR + MASA | 375.9 ± 25.8* | 406.7 ± 19.8** | 409 ± 39.4 |
| TR + NA + MASA | 331.7 ± 28.4** | 379.1 ± 24.7** | 375.8 ± 31* |

| | HDL after 1, 2 and 3 weeks, mg/dl | | |
|---|---|---|---|
| Group | HDL1 | HDL2 | HDL3 |
| Control | 54.6 ± 1.9* | 54.1 ± 1.3 | 53.7 ± 1.0* |
| TR | 76.3 ± 6.9 | 76.2 ± 11.4 | 77 ± 10.2 |
| TR + NA | 111.3 ± 9.1* | 144.7 ± 13.5# | 127.3 ± 10.9* |
| TR + MASA | 100.1 ± 9.4 | 113.8 ± 13.1 | 128.3 ± 18.5* |
| TR + NA + MASA | 112.3 ± 10.9* | 129.2 ± 13.1* | 154.1 ± 19# |

| | LDL after 1, 2 and 3 weeks, mg/dl | | |
|---|---|---|---|
| Group | LDL1 | LDL2 | LDL3 |
| Control | 18.7 ± 3.8# | 19.7 ± 4.4# | 16.3 ± 2.0# |
| TR | 388.7 ± 26.7 | 402.1 ± 19.2 | 405.1 ± 41.7 |
| TR + NA | 216.3 ± 14.0 | 250.3 ± 20.6# | 265.1 ± 18.4* |
| TR + MASA | 263.3 ± 19.4 | 287.6 ± 18.5# | 261.9 ± 12.6** |
| TR + NA + MASA | 205.7 ± 18.5#& | 222.4 ± 16.5#& | 214.4 ± 15.1$&# |

| | TG after 1, 2 and 3 weeks, mg/dl | | |
|---|---|---|---|
| Group | TG1 | TG2 | TG3 |
| Control | 38 ± 2.9# | 37 ± 3.2# | 38 ± 4.4# |
| TR | 1240 ± 80.1 | 1297 ± 78.3 | 1234 ± 114.1 |
| TR + NA | 734 ± 81.6# | 860 ± 73.8** | 828 ± 44.7* |
| TR + MASA | 964 ± 94.9* | 1079 ± 84 | 982 ± 72.7 |
| TR + NA + MASA | 721.6 ± 52.4&# | 807.6 ± 80.1&# | 714 ± 27.3&$# |

*P < 0.05 vs TR -
**<0.005 vs TR -
<0.0005 vs TR -
$P < 0.05 vs NA
&P < 0.05 vs MASA

The combined use of MASA and NA is significantly more efficient than action of substances alone.

Example 8

Influence of Test Substances on Platelet Aggregation and Formation of Thrombi 10.1. Platelet Aggregation ASA is one of the most widely used prophylactic antiplatelet agents (Miner J et al, *Tex Heart Inst J* 2007; 34(2):179-186). ASA has been combined with NA as anti-inflammatory agent (U.S. Pat. No. 3,312,593) and antiplatelet agent (WO 9632942). Many other agents and combinations thereof are known. It has been established that MD normalizes vascular tone, inhibits platelet aggregation and fatty acid oxidation, and optimizes oxygen consumption during myocardial ischemia (Tsirkin V I, *Ros Kardiol Zh* 2002; 1:45-52). NA also slightly inhibits platelet aggregation (Lakin K M et al, *Farmakol Toksikol*, 1980, 43(5):581-5 (Rus). The typical antiplatelet agent clopidogrel is used alone (U.S. Pat. No. 4,529,596, U.S. Pat. No. 4,847,265, U.S. Pat. No. 5,576,328) or in combination with statin (WO9804259) or ASA (WO9729753). Also the antiplatelet agent dipyridamole can be combined with ASA (Halkes P H et al, *Lancet* 2006, 367(9523):1665-73). The clinical experience points to higher versatility of various agent combinations.

Method.

Platelet aggregation was studied using whole blood impedance aggregometry on Multiplate (Multiple Platelet Function Analyzer, Dynabyte Medical, Germany) (Toth O et al, *Thromb Haemost* 2006; 96:781-788. Velik-Salchner C et al, *Anesth Analg* 2008; 107:1798-1806). Blood samples for in vitro experiment were collected from healthy donor B. (age 37 y.), who had not used ASA or any other antiplatelet agents, into plastic tubes covered with hirudin (Dynabyte Medical, Germany) and used for measurement between 30 min and 4 h after collection. In the ex vivo experiment blood was collected into plastic tubes covered with hirudin (Dynabyte Medical, Germany) from narcotized rats that were treated for 3 previous days with test substances p.o. The measurements were performed according to modified Dynabyte Medical protocol. Isotonic sodium chloride solution (0.3 ml, or saline with investigated compound (in final concentration $10^{-4}$ mmol/ml each of them)) was pre-heated to 37° C. and pipetted into the test cells and 0.3 ml of whole blood sample anticoagulated with hirudin was added. After 5 min incubation and stirring at 37° C., measurements were initiated by adding of the appropriate agonist solution (sourced from Dynabyte Medical, Germany):

1) adenosine diphosphate (ADP)—ADP-Test. ADP stimulates platelet activation by the ADP receptors (P2Y 12 and other).

2) arachidonic acid (AA)—ASPI-Test: activation by AA—the substrate of the cyclooxygenase forms tromboxane A2 (TXA2) which is a potent platelet agonist.

3) ADP HS test (prostaglandin $E_1$ in combination with ADP). The addition of the endogenous inhibitor $PGE_1$ make ADP HS test more sensitive towards the effects of clopidogrel and related drugs compared to ADP test.

Aggregation curves were recorded for 6 min. and analyzed using Dynabyte Medical software. We calculated the following parameters of platelet aggregation:

1) Amax, the maximal value of platelet aggregation expressed in arbitrary units (AU) of aggregation;

2) AUC, total area under the aggregation curve (AU*min). It is affected by the total height of the aggregation curve as well as by its slope and is best suited to express the overall platelet activity.

Statistics.

The results were expressed as the mean and standard error of the mean (Mean±SEM). To estimate significance of differences, one-way ANOVA was used. If null hypothesis had been rejected, the post-hoc Student-Newman-Keuls test was employed.

Results.

As shown in Table 21, MASA in concentration $10^{-4}$ mol provided significant protection against ADP and especially against platelet aggregation induced by AA and ADP+$PGE_1$ (significant reduction of AUC un Amax, Table 21). NA (in $10^{-4}$ mmol/ml group) also reduced aggregation caused by ADP (see Amax, Table 21). The combined action of both substances provided significantly higher and pronounced reduction of platelet aggregation caused by ADP or ADP+$PGE_1$, manifested both in AUC and Amax data (Table 21).

TABLE 21

MD, NA and combined influence on ADP, AA and PGE$_1$ + ADP induced platelet aggregation; Mean ± SEM; N = 5-8.

ADP

| Group | AUC (AU*min) | Amax (AU) |
|---|---|---|
| Control | 942 ± 43.7 | 169.3 ± 6.4 |
| MASA 10$^{-5}$ | 828 ± 63.5 | 153.5 ± 8.8 |
| MASA 10$^{-4}$ | 798 ± 38.9$^1$ | 140.5 ± 7.2$^1$ |
| MD 10$^{-4}$ | 869 ± 36.3 | 153.2 ± 6.1 |
| ASA 10$^{-4}$ | 883 ± 50.3 | 151.7 ± 9.3 |
| NA 10$^{-4}$ | 859 ± 62.5 | 148.0 ± 5.2$^1$ |
| MD10$^{-4}$ + NA10$^{-4}$ | 474 ± 34.9$^{3\#\#\&\$\$a}$ | 81.0 ± 5.7$^{4\#\#\#\&\$\$a}$ |
| MASA 10$^{-4}$ + NA10$^{-4}$ | 403 ± 37.5$^{3@a\$\$\&\&\#\#}$ | 75.3 ± 6.8$^{2@a\$\$\&\&\#\#}$ |
| ASA + NA | 805 ± 47.3$^{1b}$ | 137 ± 7.1$^{1b}$ |

AA

| Group | AUC (AU*min) | Amax (AU) |
|---|---|---|
| Control | 1023 ± 46.3 | 178.8 ± 6.9 |
| MASA 10$^{-5}$ | 832 ± 54.1$^1$ | 148.4 ± 5.7$^1$ |
| MASA 10$^{-4}$ | 298 ± 25.3$^{3\#\&\&\$}$ | 66.1 ± 6.8$^{3\#\&\&\$}$ |
| MD 10$^{-4}$ | 1050 ± 37.6$^\&$ | 179.5 ± 7.3$^\&$ |
| ASA 10$^{-4}$ | 450 ± 24.8$^{2\#@}$ | 103.1 ± 5.9$^{2\#@}$ |
| NA 10$^{-4}$ | 1010 ± 41.7 | 161.1 ± 9.4 |
| MD10$^{-4}$ + NA10$^{-4}$ | 1106 ± 55.4 | 173.3 ± 12.1 |
| MASA 10$^{-4}$ + NA10$^{-4}$ | 216 ± 18.7$^{4@ab\$\$\#\#\&\&\&}$ | 48.5 ± 6.9$^{4@ab\$\$\#\#\&\&\&}$ |
| ASA + NA | 463 ± 35.2$^{2b\$\#}$ | 99.4 ± 8.2$^{2b\$\#}$ |

PGE$_1$ + ADP

| Group | AUC (AU*min) | Amax (AU) |
|---|---|---|
| Control | 1005 ± 46.5 | 175.3 ± 8.9 |
| MASA 10$^{-5}$ | 595 ± 45.3$^1$ | 99.3 ± 4.8$^2$ |
| MASA 10$^{-4}$ | 533 ± 20.3$^{3\$\&\&\&}$ | 87.7 ± 4.6$^{3\$\&\&\&}$ |
| MD 10$^{-4}$ | 587 ± 37.4$^{2\&\&}$ | 101.4 ± 2.2$^{2\&\&}$ |
| ASA 10$^{-4}$ | 961 ± 35.0 | 162.5 ± 8.7 |
| NA 10$^{-4}$ | 862 ± 51.9 | 146.7 ± 8.6 |
| MD10$^{-4}$ + NA10$^{-4}$ | 306 ± 35.5$^{3\#\$a\&\&\&}$ | 54.5 ± 5.8$^{3\#\$a\&\&\&}$ |
| MASA 10$^{-4}$ + NA10$^{-4}$ | 296 ± 28.7$^{4@a\$\#\&\&\&}$ | 50.2 ± 7.3$^{3@a\$\$\#\&\&\&}$ |
| ASA + NA | 603 ± 42.5$^{1\$b\&}$ | 98.0 ± 7.2$^{2\$b\&}$ |

$^1$P < 0.05 vs Control -
$^2$P < 0.005 vs Control -
$^3$P < 0.0005 vs Control -
$^4$P < 0.00005 vs Control
$^\&$P < 0.05 vs ASA -
$^{\&\&}$P < 0.005 vs ASA -
$^{\&\&\&}$P < 0.0005 vs ASA -
$^\#$P < 0.005 vs MD 10$^{-4}$
$^{\#\#}$P < 0.0005 vs MD 10$^{-4}$ -
$^\$$P < 0.005 vs NA 10$^{-4}$ -
$^{\$\$}$P < 0.0005 vs NA 10$^{-4}$ -
$^@$P < 0.05 vs MASA 10$^{-4}$ -
$^a$P < 0.05 vs ASA + NA -
$^b$P < 0.05 vs MD + NA MASA significantly better than ASA or MD protected from platelet aggregation induced by AA (Table 21). The combination MASA+NA displayed significantly higher activity against aggregation induced by AA, surpassing that of each substance separately, as well as that of ASA+NA and MD+NA (Table 21).

Parallel experiments were conducted with dipyridamole (DI) and combination of DI with ASA or MASA on ADP or AA caused platelet aggregation (Table 22). DI displays anti-thrombotic and anti-aggregatory activity (Mammen E F, *Thrombosis Research Supplement* 1990 XII, 1-3). Dipyridamole plus aspirin versus aspirin alone is more effective after cerebral ischaemia of arterial origin (Halkes P H et al. Lancet 2006, 367(9523):1665-73).

TABLE 22

Influence of test substances separately and in combination on platelet aggregation induced by ADP or AA. Mean ± SEM; N = 5-8.

| | ADP | | AA | |
|---|---|---|---|---|
| Group | AUC (AU*min) | Amax (AU) | AUC (AU*min) | Amax (AU) |
| Control | 942 ± 43.7 | 169.3 ± 6.4 | 1023 ± 46.3 | 178.8 ± 6.9 |
| MASA 10$^{-4}$ | 798 ± 38.9$^1$ | 140.5 ± 7.2$^1$ | 298 ± 25.3$^{3aa\&}$ | 66.1 ± 6.8$^{3aa\&}$ |
| ASA 10$^{-4}$ | 883 ± 50.3 | 151.7 ± 9.3 | 450 ± 24.8$^{3a@}$ | 103.1 ± 5.9$^{2a@}$ |
| DI 3 × 10$^{-4}$ | 665 ± 44.1$^{2\&}$ | 111.1 ± 6.9$^{2\&}$ | 1104 ± 45.5$^{\&@@}$ | 173.9 ± 5.2$^{\&@@}$ |
| MASA 10$^{-4}$ + DI 3 × 10$^{-4}$ | 465 ± 27.0$^{3@\$a\&}$ | 69.7 ± 3.2$^{3@\$a\&}$ | 116 ± 9.8$^{4@@\$\$aaa\&}$ | 38.5 ± 3.6$^{4@@\$\$aaa\&}$ |
| ASA 10$^{-4}$ + DI 3 × 10$^{-4}$ | 667 ± 39.4$^{2\&}$ | 105.2 ± 6.7$^{2\&@}$ | 207.9 ± 27.5$^{3\&aa}$ | 62.8 ± 6.8$^{2\&aa}$ |

$^1$P < 0.05 vs Control -
$^2$P < 0.005 vs Control -
$^3$P < 0.0005 vs Control
$^4$P < 0.00005 vs Control -
$^\&$P < 0.05 vs ASA -
$^@$P < 0.05 vs MASA
$^{@@}$P < 0.005 vs MASA -
$^a$P < 0.05 vs DI -
$^{aa}$P < 0.005 vs DI -
$^{aaa}$P < 0.0005 vs DI
$^\$$P < 0.05 vs ASA + DI -
$^{\$\$}$P < 0.005 vs ASA + DI In this series the highest activity was displayed by MASA+DI that was significantly higher than that of ASA+DI (Table 22).

8.2. Thrombosis

Two weeks long therapeutic use of MD peroral administration in rabbits and dogs after experimental arterial thrombosis showed trombolytic effect (Logunova L et al, *Experim Clin Pharmacoter* 1991; 19:91-98 (Rus). No data on prophylactic effect of MD on limitation or prevention of thrombosis are known. Through a variety of mechanisms, NA reduces thrombosis (Rosenson R S et al, *Atherosclerosis* 1998; 140: 271-80).

Method.

We chose an experimental thrombosis model based on rat arterial thrombosis induced by $FeCl_3$ (Kurz K et al, *Thromb Res* 1990, 60:269-280. Wang X, Xu L, *Thromb Res* 2005,115: 95-100). Tissue damage initiated by iron-mediated chemical oxidation predisposes the injured area to platelet adherence and aggregation followed by coagulation activation and fibrin deposition. Male Wistar rats with mass 350-420 g were used in experiments. Animals were kept in groups of 7-8 in adequate cages in climatized room at 22±1° C., relative humidity 60±5% and 12/12-hour light/darkness cycle with free access to feed and water. All experiments were carried out in accordance with the European Community Council's Directive of 24 Nov. 1986 (86/609/EEC) relative to experimental animal care. All efforts were made to minimize animal suffering and to reduce the number of animals used. Rats were randomly divided into various experimental groups, each consisting of not less than seven animals. The vehicle or test compound MD (25 mg/kg), NA (25 mg/kg), MASA (10 mg/kg), ASA (5 mg/kg) and combination MD+NA (25+25 mg/kg), MASA+NA (10+25 mg/kg) and ASA+NA (5+25 mg/kg) was administered by oral route 2 h before the initiation of thrombosis. Parallel experiments were conducted to compare the effects of a single dose of test substance (given 2 h before the initiation of thrombosis) and repeated doses (once daily for 3 days). Groups of 7-8 animals received the following substances: MASA (10 mg/kg), clopidogrel (CL) (5 mg/kg), ASA (5 mg/kg) and combination MASA+CL (10+5 mg/kg) or ASA+CL (5+5 mg/kg). Rats were anaesthetized with pentobarbital sodium (50 mg/kg, i.p. and 10 mg/kg/h) and were placed on a heat controlled operating table throughout the experiment to maintain a body temperature of 37° C. One of the carotid arteries was exposed by cervical incision, separated from the adherent tissue, vagus nerve, and a flow probe (electromagnetic blood flow meter MFV 1200, Nicon Kohden, Japan) was placed on the exposed segment of common carotid artery to record the blood flow. After a stabilization period of 15 min, thrombosis was induced by topically applying (in contact with the adventitial surface of vessel) two pieces (2×1 mm) of Whatman filter paper, soaked in 15% solution of $FeCl_3$. Thrombosis time of carotid artery was recorded as time taken for the complete cessation of the blood flow and has been reported as time till occlusion (TTO). If the blood flow did not cease within 90 min in the active treatment group, TTO was recorded as >90 min.

Additionally during the thrombosis experiment rat tail bleeding time was measured. The tail was transected 5 mm from the tip with scalpel and the tail was immediately immersed into 37° C. warm isotonic saline until termination of bleeding was noted. Termination of bleeding was defined as the time of complete stop of bleeding with no recurrence of bleeding within the next 30 s.

After the thrombosis experiment the narcotized animals who received test substances for 3 days were used for platelet aggregation test ex vivo. The abdomen was opened and blood from vena cava inferior collected into plastic tubes covered with hirudin (Dynabyte Medical, Germany).

Blood samples were used for measurement between 30 min and 4 h after collection. The measurements were performed according to modified Dynabyte Medical protocol (see above under Platelet aggregation).

Statistics.

The results were analyzed by Microsoft Excel 2007 software. Data are presented as means±SEM. Differences between experimental groups were compared using one-way ANOVA with repeated comparisons (Tukey's test). P<0.05 was considered as significant.

Results.

The average time for $FeCl_3$ caused vessel thrombosis and the resulting arterial flow arrest in control group was 24.4 min (Table 23).

TABLE 23

Influence of test substances on $FeCl_3$ induced carotid artery thrombosis. Mean ± SEM; N = 7-8

| Group | Time till occlusion | | Tail bleeding time | |
|---|---|---|---|---|
| | min | % | min | % |
| Control | 24.4 ± 1.45 | 100 | 8.9 ± 1.28 | 100 |
| NA (25 mg/kg) | 30.3 ± 3.12 | 124 | 11.5 ± 1.39 | 129 |
| MD (25 mg/kg) | 29.8 ± 2.29 | 122 | 10.5 ± 1.01 | 118 |
| MD + NA (25 + 25 mg/kg) | 34.0 ± 2.78[1] | 139 | 11.4 ± 1.42 | 128 |
| MASA (10 mg/kg) | 41.7 ± 3.95[2#] | 171 | 12.1 ± 2.20 | 136 |
| MASA + NA (10 + 25 mg/kg) | 53.1 ± 4.12[2$abc#] | 218 | 13.5 ± 4.19 | 152 |
| ASA (5 mg/kg) | 35.2 ± 3.02[1] | 144 | 13.8 ± 3.27 | 155 |
| ASA + NA (5 + 25 mg/kg) | 42.5 ± 4.24[2$#] | 174 | 15.2 ± 2.12[1] | 171 |

[1]P < 0.05 vs Control -
[2]P < 0.005 vs Control -
[#]P < 0.05 vs MD -
[$]P < 0.05 vs NA
[a]P < 0.05 vs ASA -
[b]P < 0.05 vs ASA + NA -
[c]P < 0.05 vs MD + NA Prophylactic treatment with MASA provided significant prolongation of TTO (P<0.005 vs Control), but contrary to ASA was considerably less efficient in bleeding test (136 to 155%). MASA+NA (10+25 mg/kg) caused comparatively longer delay of thrombosis, surpassing that of MD+NA or ASA+NA (Table 23). It should be noted that using ASA and ASA+NA, the increase of the TTO parallels that of bleeding time, while the increase of TTO using MASA or MASA+NA is considerably higher than that of the bleeding time (Table 23).

In parallel experiments with common control the influence on thrombosis was investigated for ASA, MASA and CL and combinations thereof. The test substances were applied as single dose (2 h before testing) or given once a day for 3 days. ASA or CL, introduced 2 hours before the thrombosis test significantly prolonged TTO vs control group that received water (Table 24).

TABLE 24

Influence of single dose of test substances on TTO and bleeding time in FeCl$_3$ induced carotid artery thrombosis experiment. Mean ± SEM; N = 7-8

| Group | Time till occlusion min | % | Tail bleeding time min | % |
|---|---|---|---|---|
| Control | 24.4 ± 1.45 | 100 | 8.9 ± 1.28 | 100 |
| MASA (10 mg/kg) | 41.7 ± 3.95[2b] | 171 | 12.1 ± 2.20 | 136 |
| ASA (5 mg/kg) | 35.2 ± 3.02[1] | 144 | 13.8 ± 3.27 | 155 |
| CL (5 mg/kg) | 31.7 ± 2.40[1] | 130 | 11.9 ± 3.62 | 134 |
| MASA + CL (10 + 5 mg/kg) | 61.5 ± 4.31[3$abc] | 252 | 15.7 ± 3.16 | 176 |
| ASA + CL (5 + 5 mg/kg) | 45.4 ± 4.80[2ab] | 186 | 16.3 ± 2.25[1] | 183 |

[1]P < 0.05 vs Control -
[2]P < 0.005 vs Control -
[3]P < 0.005 vs Control
[$]P < 0.05 vs MASA -
[a]P < 0.05 vs ASA -
[b]P < 0.05 vs CL -
[c]P < 0.05 vs ASA + CL Single dose of MASA provided more significant increase of TTO than CL. MASA given together with CL significantly increased TTO but only slightly changed the bleeding time (Table 24). It should be noted that combination MASA+CL caused significant increase of TTO compared with that of separate substances and that of combination ASA+CL. The repeated treatment with test substances caused further increase of TTO and bleeding time (Table 25).

TABLE 25

Influence of repeated treatment by test substances on TTO and bleeding time in FeCl$_3$ induced carotid artery thrombosis experiment. Mean ± SEM; N = 7-8

| Group | Time till occlusion min | % | Tail bleeding time min | % |
|---|---|---|---|---|
| Control | 25.3 ± 1.75 | 100 | 8.6 ± 1.37 | 100 |
| MASA (10 mg/kg/d) | 48.4 ± 4.35[2] | 191 | 13.1 ± 2.63 | 152 |
| ASA (5 mg/kg/d) | 40.9 ± 3.25[1] | 162 | 17.8 ± 3.17[1] | 207 |
| CL (5 mg/kg/d) | 49.1 ± 7.75[1] | 194 | 18.3 ± 3.78[1] | 213 |
| MASA + CL (10 + 5 mg/kg/d) | 64.6 ± 8.01[2a$] | 255 | 20.7 ± 3.88[1] | 241 |
| ASA + CL (5 + 5 mg/kg/d) | 61.0 ± 10.32[2a] | 241 | 27.4 ± 4.98[2$a] | 319 |

[1]P < 0.05 vs Control -
[2]P < 0.005 vs Control -
[$]P < 0.05 vs MASA -
[a]P < 0.05 vs ASA Repeated treatment with MASA or CL produced significantly higher influence on TTO than ASA (correspondingly, 191 and 194% against 162%), but MASA contrary to CL or ASA did not increase the bleeding time (Table 25). The repeated treatment with MASA+CL or ASA+CL produced considerable and rather similar increase of TTO, but MASA+CL comparatively less than ASA+CL (241% vs 319%) influenced the tail bleeding time (Table 25).

Experiments Ex Vivo

After the thrombosis experiment animal blood was collected and aggregation parameters were measured. Three days long treatment by MASA in dose 10 mg/kg caused significant reduction of platelet aggregation by all tested aggregation inducers (Table 26).

TABLE 26

Influence of MASA, ASA, CL and combinations thereof on platelet aggregation ex vivo; Mean ± SEM; N = 4-7.

| | ADP | |
|---|---|---|
| Group | AUC (AU*min) | Amax (AU) |
| Control | 794 ± 33.5 | 149.7 ± 9.4 |
| MASA 10 mg/kg/d | 528 ± 46.5[1] | 75.5 ± 12.8[2] |
| ASA 5 mg/kg/d | 768 ± 53.2 | 150.3 ± 13.5 |
| CL 5 mg/kg/d | 423 ± 39.4[2&] | 68.2 ± 15.1[2&] |
| MASA + CL (10 + 5 mg/kg/d) | 140 ± 16.8[3@&&&ab] | 35.3 ± 9.4[3@&&&ab] |
| ASA + CL (5 + 5 mg/kg/d) | 230 ± 29.8[3&&a] | 53.3 ± 11.5[2&] |

| | AA | |
|---|---|---|
| Group | AUC (AU*min) | Amax (AU) |
| Control | 935 ± 62.3 | 167.8 ± 11.6 |
| MASA 10 mg/kg/d | 232 ± 44.1[2&a] | 48.2 ± 9.7[3&a] |
| ASA 5 mg/kg/d | 550 ± 31.3[2] | 86.1 ± 6.8[2] |
| CL 5 mg/kg/d | 905 ± 53.5[&] | 160.7 ± 13.5[&@] |
| MASA + CL (10 + 5 mg/kg/d) | 187 ± 29.4[3&&a] | 30.7 ± 9.8[3&&a] |
| ASA + CL (5 + 5 mg/kg/d) | 239 ± 32.7[2&a] | 39.8 ± 14.1[2&a] |

| | PGE$_1$ + ADP | |
|---|---|---|
| Group | AUC (AU*min) | Amax (AU) |
| Control | 855 ± 40.5 | 159.5 ± 12.2 |
| MASA 10 mg/kg/d | 195 ± 35.3[3] | 41.4 ± 14.8[2] |
| ASA 5 mg/kg/d | 794 ± 48.6 | 147.2 ± 11.8 |
| CL 5 mg/kg/d | 259 ± 49.3[2&] | 49.7 ± 9.9[3&] |
| MASA + CL (10 + 5 mg/kg/d) | 87 ± 15.8[3@ab&&&] | 15.5 ± 4.8[3@ab&&&] |
| ASA + CL (5 + 5 mg/kg/d) | 128 ± 19.4[2@a&&&] | 24.6 ± 5.8[3@a&&&] |

[1]P < 0.05 vs Control -
[2]P < 0.005 vs Control -
[3]P < 0.0005 vs Control -
[@]P < 0.05 vs MASA
[&]P < 0.05 vs ASA -
[&&]P < 0.005 vs ASA -
[&&&]P < 0.0005 vs ASA -
[a]P < 0.05 vs CL -
[b]P < 0.05 vs ASA + CL Treatment by CL in dose 5 mg/kg/d for 3 days caused considerable protection against the aggregation induced by ADP and PGE$_1$+ADP, but did not protect from aggregation induced by AA. ASA provided significant protection against aggregation induced by AA, but was not effective against ADP and PGE$_1$+ADP (Table 26). The combination of MASA and CL (10+5 mg/kg/d×3) provided comparatively highest prevention from aggregation caused by various agents, significantly better than that provided by ASA+CL in ADP and PGE$_1$+ADP tests (Table 26).

Summary

MASA considerably better than MD or ASA in similar molar concentrations protects against platelet aggregation induced by AA. Protection by MASA+NA significantly surpasses that of MD, NA and ASA, as well as combination ASA+NA against all inducers of aggregation, and MD+NA against aggregation induced by AA.

Considering the positive effect of MASA and MASA+NA combination against platelet aggregation and extension of TTO in vivo, MASA or MASA+NA combination can find application for reducing platelet aggregation and thrombosis risk in patients with pronounced atherosclerosis, potential myocardial infarction and insult, as well as disturbances of peripheral circulation. The fact that MASA and MASA+NA combination does not prolong tail bleeding time indicates the possible use of this combination for patients with increased bleeding risk in pre- and postoperation period.

MASA+DI considerably better than ASA+DI protects against aggregation induced by ADP and AA.

MASA+CL. In the thrombosis experiment a single dose of MASA+CL provides better protection against $FeCl_3$ induced thrombosis than ASA+CL. MASA+CL comparatively less than ASA+CL prolongs tail bleeding time. In the ex vivo experiment MASA+CL provides considerably more pronounced protection against platelet aggregation than CL, ASA or MASA. MASA+CL better than ASA+CL protects against platelet aggregation induced by ADP and $PGE_1$+ADP.

These facts indicate that MASA+CL could find application in clinic for immediate protection against increased platelet aggregation risk, imminent or ongoing thrombosis.

Example 9

Comparative Investigation of Combined Application of MASA/NA, MD/NA and LA/NA for Reduction of NA Induced Flushing Nicotinic acid (niacin, NA) effectively lowers serum cholesterol, LDL and triglycerides, while raising HDL. However a limiting adverse effect in patients receiving immediate- or sustained-release niacin is the rapid development of significant cutaneous warmth and vasodilatation, referred to as "flush" which severely leading to discontinuation (Gupta E K, Ito M K, Heart Dis 2002; 4:124-137). Laropiprant (MK-0524) (LA) has been proposed as one of the most active and perspective agent for reducing NA flushing (Cheng K et al, PNAS 2006; 103:6682-6687).

9.1. Antagonism to Cutaneous Vasodilatation, Caused by Nicotinic Acid

Model. Male Wistar rats were narcotized by sodium pentobarbital (50 mg/kg i.p.) and kept under narcosis by additional doses (10 mg/kg) each hour. Blood pressure was measured in left carotid artery, ECG recorded by standard II lead. Blood flow in the right ear artery was measured by laser Doppler flow meter (OXYFLOW 2000, USA). Blood flow, ECG and arterial pressure were registered by AD Instruments PowerLab systems and stored in computer for further processing. After 10 min. long registration of baseline test substances were injected s.c. into withers area and registration continued for 30 min. The average blood flow data for each animal were calculated taking into account the average blood pressure and compared with initial and control. Results were calculated from 5 to 8 separate experiments and expressed in % as maximal change in blood flow to baseline (Carballo-Jane E et al, J Pharmacol Toxicol Methods 2007; 56(3):308-316).

Statistics.

The results are presented as means±SEM for each group. Statistical analysis within groups was performed by Student t-Test. Differences between each experimental group were compared using one-way ANOVA with repeated comparisons (Tukey's test). P<0.05 was considered as significant.

Results.

Nicotinic acid (NA) in dose 15 mg/kg caused significant increase in blood flow in ear artery in this animal model (Table 27). MASA, similarly to control (buffered 0.9% NaCl solution), caused non-significant variation in blood flow. NA together with MASA caused delayed (slowly increasing) and statistically significant less pronounced absolute increase in blood flow as compared to NA alone (Table 27). So we have unexpectedly found that MASA significantly reduces peripheral vasodilatation caused by NA. The potential of MASA to antagonize the peripheral vasodilatation, caused by NA may have beneficial effect in clinic for diminishing the cutaneous effects (flushing) of nicotinic acid and was further investigated in detail as described below.

TABLE 27

Influence of experimental substances on cutaneous vasodilatation; Mean ± SEM, N = 5-8

| Group | Changes in blood flow, % |
|---|---|
| Control | 2.92 ± 2.76 |
| NA (15 mg/kg) | 55.75 ± 11.5** |
| MASA (45 mg/kg) | 8.04 ± 2.02$ |
| NA + MASA (15 mg/kg + 45 mg/kg) | 25.91 ± 9.52*$ |

*P < 0.05 vs Control -
**P < 0.005 vs Control -
$P < 0.05 vs NA 9.2. Antagonism to Cutaneous Temperature Raising, Caused by Nicotinic Acid The objective of our investigation was comparing the effect of MASA, MD and LA on flushing (changes of skin temperature) caused by NA in experiment.

Methods.

Male Wistar rats (280-330 g) were used. Animals were held in groups of 6 in climatized rooms at 22±1° C., relative humidity 60±5%, and 12/12-hour light/dark cycle with free access to drinking water and feed (R3—Lactamin AB, Sweden). For registration of changes in skin temperature of intact rats contactless temperature recording method was used (Papaliodis D et al, Br J Pharmacol 2008; 153:1382-1387). Temperature measurements were performed with a hand-held infrared thermometer (Model Proscan 510, TFA-Dostman). Animals were habituated to handling and to the infrared probe for 3 days before use. Temperature readings from the dorsal side of each ear were recorded without anaesthesia at beginning and during experiment. The ear temperature was measured every 5 min. for a period of up to 60 min. The animals were returned to their cages between measurements. NA, MD and MASA were dissolved in saline and pH was corrected immediately before usage. LA (MK 0524, Cayman Chemicals) was first dissolved in DMSO and then freshly diluted with 0.9% NaCl, on each day of the experiment. The rate of NA and LA combination was based on Summary of Product Characteristics for Tredaptive™ (nicotinic acid/laropiprant) 1000 mg/20 mg modified-release tablets.

Statistics.

Six ear temperature measurements (three from each ear) were averaged for each time point. Data were analyzed by Microsoft Excel software and results expressed as mean±standard error of mean (Mean±SEM). Mean results of different groups were compared using single-factor analysis according to ANOVA and t-Student's test. P<0.05 was considered as significant.

9.2.1. Testing of Time and Solvent Influence on Skin Temperature

| GROUP | TREATMENT | Number of animals |
|---|---|---|
| SolvLA | Solvent for LA | 6 |
| SolvNA | Solvent for NA, MASA and MD | 6 |
| NA | NA 15 mg/kg sc | 6 |

9.2.2. Investigation of Separate Test Substances on Skin Temperature at Simultaneous [0] or 30 Min Advance [30] s.c. Administration The influence of LA, MD or MASA alone on skin temperature was checked. Each investigated compound was introduced s.c. simultaneously with NA as LA+NA [0] or 30 min in advance to NA as LA+NA [30].

| GROUP | TREATMENT | Number of animals |
|---|---|---|
| Control/solvent | | 6 |
| NA | NA 15 mg/kg | 6 |
| LA | LA 0.3 mg/kg | 6 |
| LA + NA | LA 0.3 mg/kg + NA 15 mg/kg | 6 |
| MD | MD 45 mg/kg | 6 |
| MD + NA | MD 45 mg/kg + NA 15 mg/kg | 6 |
| MASA | MASA 45 mg/kg | 6 |
| MASA + NA | MASA 45 mg/kg + NA 15 mg/kg | 6 |

9.2.3. Investigation of the Effect of MASA/NA and MD/NA Combination on Skin Temperature at Simultaneous [0] or 45 Min Advance [45] p.o. Administration

| GROUP | TREATMENT | Number of animals |
|---|---|---|
| Control/solvent | | 6 |
| NA | NA 40 mg/kg | 8 |
| MD | MD 100 mg/kg | 6 |
| MD + NA | MD 100 mg/kg + NA40 mg/kg | 6 |
| MASA150 | MASA 150 mg/kg | 6 |
| MASA75 + NA | MASA 75 mg/kg + NA 40 mg/kg | 6 |
| MASA150 + NA | MASA 150 mg/kg + NA 40 mg/kg | 6 |

Results

R 9.2.1 Testing of Time and Solvent Influence on Skin Temperature

The baseline mean ear temperature was 28.4-30.6° C. recorded at 10 AM to 2 PM. A time response study for NA (15 mg/kg s.c.) showed a maximal temperature increase of 2.32±0.37° C. from baseline and 2.57±0.43 in comparison with Solvent group (P<0.005) at 10 min as shown in FIG. 1. It was established that the effect of the LA solvent on ear temperature was substantially different from that of NA, MASA and MD solvent only in the first 5 min. after injection, therefore only one control group was used in calculation of temperature at 10 min.

R 9.2.2. Investigation of Separate Test Substances on Skin Temperature at Simultaneous [0] or 30 Min Advanced [30] s.c. Administration Subcutaneous injection of MASA, MD or LA did not cause significant changes in rat ear skin temperature (Table 28). There was no difference on temperature between the MD+NA [0], when MD was added together with NA, and MD+NA [30], when MD was given 30 min in advance of NA.

TABLE 28

Influence of MASA, LA and MD on rise of skin temperature, caused by NA; N = 6, Mean ± SEM

| Group | Initial temperature ° C. | Maximum temperature ° C. | Increase, % |
|---|---|---|---|
| Control/solvent | 29.5 ± 0.29 | 29.62 ± 0.25$$$ | — |
| NA | 29.61 ± 0.40 | 32.2 ± 0.42*** | 100 |
| MASA | 29.3 ± 0.35 | 29.2 ± 0.38$$$ | — |
| MASA + NA [0] | 29.9 ± 0.31 | 31.5 ± 0.40** | 62 |
| MASA + NA [30] | 29.6 ± 0.32 | 30.9 ± 0.32*$ | 50 |
| LA | 29.43 ± 0.27 | 29.5 ± 0.35$$$ | — |
| LA + NA [0] | 29.72 ± 0.31 | 31.45 ± 0.40** | 67 |
| LA + NA [30] | 29.51 ± 0.32 | 30.73 ± 0.34*$ | 47 |
| MD 45 | 29.42 ± 0.38 | 29.6 ± 0.31$$$ | — |
| MD + NA [0] | 29.53 ± 0.29 | 31.33 ± 0.48* | 69 |
| MD + NA [30] | 29.68 ± 0.26 | 31.40 ± 0.39* | 65 |

*P < 0.05 vs Control -
**P < 0.005 vs Control -
***P < 0.0005 vs Control
$P < 0.05 vs NA -
$$$P < 0.0005 vs NA Simultaneous administration of NA and MASA (NA+MASA [0] group; advance time=0) caused reduction of NA flushing that was similar to that caused by simultaneous administration of NA and LA or NA and MD. The increase of temperature, caused by NA was reduced, correspondingly from 100% (effect of NA) to 62%, 67 and 69% (Table 28). In our experiment administration of MASA+NA and LA+NA (when given s.c. 30 min in advance of NA), caused significant and similar protection against the increase of skin temperature, induced by NA (Table 28).

R 9.2.3. Investigation of the Effect of NA/MASA and NA/MD Combination on Skin Temperature at Oral Administration Oral (p.o.) NA introduction in dose 40 mg/kg caused substantial and prolonged (up to 60 min.) increase of rat ear skin temperature with the maximum between 15 and 45 min. (Table 29).

TABLE 29

Influence of MASA or MD on NA induced skin hyperthermia by simultaneous [0] or advance [45] treatment; N = 6-8, Mean ± SEM

| Group | Initial temp. ° C. | Temp. 15 min | Temp. 30 min | Temp. 45 min | Max incr. % |
|---|---|---|---|---|---|
| Control/solvent | 29.9 ± 0.32 | 30.2 ± 0.48$$ | 30.0 ± 0.33$$$ | 30.1 ± 0.37$$ | 9 |
| NA | 30.0 ± 0.41 | 32.3 ± 0.46** | 33.1 ± 0.41*** | 32.4 ± 0.48** | 100 |
| MASA150 | 29.7 ± 0.28 | 29.9 ± 0.33$$ | 29.5 ± 0.35$$$ | 29.6 ± 0.39$$ | 6 |
| MASA75 + NA [0] | 29.7 ± 0.33 | 31.9 ± 0.51* | 32.3 ± 0.37**$ | 32.1 ± 0.46* | 84 |
| MASA150 + NA [0] | 29.8 ± 0.37 | 30.9 ± 0.47$ | 32.0 ± 0.42*$ | 31.95 ± 0.38* | 70 |
| MD | 29.9 ± 0.35 | 30.1 ± 0.39$$ | 29.8 ± 0.38$$$ | 30.0 ± 0.34$$ | 6 |
| MD + NA [0] | 29.6 ± 0.26 | 31.3 ± 0.35*$ | 32.5 ± 0.42** | 32.2 ± 0.40* | 96 |
| MD100 + NA [45] | 29.3 ± 0.35 | 31.2 ± 0.33*$ | 32.3 ± 0.41** | 32.1 ± 0.44* | 95 |

TABLE 29-continued

Influence of MASA or MD on NA induced skin hyperthermia by simultaneous [0] or advance [45] treatment; N = 6-8, Mean ± SEM

| Group | Initial temp. °C. | Temp. 15 min | Temp. 30 min | Temp. 45 min | Max incr. % |
|---|---|---|---|---|---|
| MASA75 + NA [45] | 29.4 ± 0.30 | 31.3 ± 0.53* | 31.9 ± 0.45$ | 31.5 ± 0.42*$ | 80 |
| MASA150 + NA[45] | 29.7 ± 0.38 | 30.7 ± 0.41$ | 31.2 ± 0.44$# | 30.2 ± 0.38$$#&@ | 48 |

*P < 0.05 vs Control -
**P < 0.005 vs Control -
***P < 0.0005 vs Control
$P < 0.05 vs NA -
$$P < 0.005 vs NA -
$$$P < 0.0005 vs NA
&P < 0.05 vs MASA150 + NA [0] -
@P < 0.05 vs MASA75 + NA [45]
P < 0.05 vs MD + NA [45]

Oral introduction of MASA or MD did not cause substantial changes in skin temperature. Simultaneous introduction p.o. of MASA and NA [0] in dose 75 mg/kg caused small, but in dose 150 mg/kg substantial protection from increase of skin temperature induced by NA (Table 29). MD (100 mg/kg) when introduced simultaneously with NA protected from the increase of temperature for 15 min, but did not provide significant protection from the maximal increase of skin temperature, induced by NA (see temperature at 30 min, 45 min, Table 28). Analysis of results show that MASA in dose 150 mg/kg introduced simultaneously NA reduced the increase of skin temperature to 70% that is substantially better than reduction by NA+MD (96%). The increase by NA alone is regarded as 100%. Introducing substances in preventive mode—45 min before NA, the temperature lowering action of MASA150+NA [45] increased and was significantly better than that of MD+NA [45] or MASA75+NA [45] (Table 28).

MASA when introduced p.o. or s.c. reduces the increase of skin temperature induced by NA. When introduced s.c. MASA similarly to laropiprant reduced the increase of skin temperature induced by NA both at simultaneous and preventive use. The substantial anti-flushing activity of MASA when introduced p.o. together with NA or in preventive mode, indicates the potential usefulness of MASA for reducing the undesirable cutaneous effects of NA (flushing).

SUMMARY CONCLUSIONS

Since MASA has anti-inflammatory, antihyperlipidemic and antiplatelet effects it can be considered as a novel therapeutic agent for the treatment of thrombosis disorders.

MODES OF CARRYING OUT THE INVENTION

The present invention provides a medicinal product comprising MASA for use as antiinflammatory, analgesic, antipyretic, antirheumatic, antihyperlipidemic, antiatherosclerotic, antiaggregative and antithrombotic agent. The medicinal product of the invention may be administered in the form of a pharmaceutical composition. According to this aspect of the invention there is provided a pharmaceutical composition which comprises MASA in admixture with a pharmaceutically acceptable diluent or carrier.

Since the antiinflammatory, analgesic, antipyretic, antirheumatic, antihyperlipidemic, antiatherosclerotic, antiaggregative and antithrombotic use of the medicinal product presumes prolonged use, the most preferable mode of carrying out the invention is provided by a form suitable for oral use, for example as tablets or capsules.

According to a further aspect of the invention there is provided the use of the medicinal product as defined herein before or of the pharmaceutical composition as defined hereinbefore, for the manufacture of a medicament for the treatment of inflammation, pain, fever, rheumatic conditions, hyperlipidemic condition, atherosclerotic condition, platelet aggregation or thrombi formation.

A further aspect of the invention concerns combination medicinal products comprising MASA and another agent selected from the group of NA, statins, CL and DI. These products can be based on pharmaceutical compositions developed for MASA itself.

The invention claimed is:

1. A compound which is a 3-(trimethylammonioamino) propanoate (meldonium) acetylsalicylic acid addition salt, wherein the compound exhibits essentially the following X-ray pattern having peaks at $2\Theta$ values 5.19, 13.22, 13.82, 14.20, 14.95, 15.36, 15.93, 18.11, 18.97, 19.74, 21.02, 22.15, 23.15, 23.65, 24.31, 25.28, 26.18, 26.58, 27.73, 28.36±0.2°.

2. A pharmaceutical composition comprising the compound of claim 1 and a pharmaceutically acceptable carrier.

3. The pharmaceutical composition of claim 2, which is an immediate-release, sustained-release or extended-release formulation.

4. The pharmaceutical composition of claim 2, which is an oral dosage form.

5. A composition comprising a combination of a therapeutically effective amount of the compound of claim 1 and a therapeutically effective amount of nicotinic acid or pharmaceutically acceptable salt thereof.

6. The composition of claim 5, wherein the compound of claim 1 is in the form of an immediate-release, sustained-release or extended-release formulation.

7. The composition of claim 5, wherein the nicotinic acid or pharmaceutically acceptable salt thereof is in the form of an immediate-release, sustained-release or extended-release formulation.

8. A composition comprising a combination of a therapeutically effective amount of a compound of claim 1 and a statin selected from atorvastatin, cerivastatin, fluvastatin, lovastatin, mevastatin, pitavastatin, pravastatin, rosuvastatin and simvastatin.

* * * * *